(12) United States Patent
Rus et al.

(10) Patent No.: US 8,227,194 B2
(45) Date of Patent: Jul. 24, 2012

(54) MONOCLONAL ANTIBODIES WITH BINDING SPECIFICITY FOR RESPONSE GENE TO COMPLEMENT 32 (RGC-32)

(75) Inventors: Horea Rus, Cantonsville, MD (US); Tudor Constantin Badea, Cockeysville, MD (US); Matthew Fosbrink, Ellicott City, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 1091 days.

(21) Appl. No.: 11/911,103

(22) PCT Filed: Apr. 10, 2006

(86) PCT No.: PCT/US2006/013476
§ 371 (c)(1),
(2), (4) Date: May 27, 2008

(87) PCT Pub. No.: WO2006/110748
PCT Pub. Date: Oct. 19, 2006

(65) Prior Publication Data
US 2011/0034344 A1 Feb. 10, 2011

Related U.S. Application Data

(60) Provisional application No. 60/669,463, filed on Apr. 8, 2005.

(51) Int. Cl.
*G01N 33/53* (2006.01)
*G01N 33/554* (2006.01)
*G01N 33/563* (2006.01)
*G01N 33/577* (2006.01)
*G01N 33/68* (2006.01)
*C07K 16/18* (2006.01)

(52) U.S. Cl. .......... 435/7.1; 435/40.5; 436/501; 436/63; 530/387.1; 530/388.1; 530/388.85

(58) Field of Classification Search .................... 435/7.1, 435/40.5; 436/501, 63; 530/387.3, 388.1, 530/388.85
See application file for complete search history.

(56) References Cited

U.S. PATENT DOCUMENTS 5,618,920 A 4/1997 Robinson et al.
6,323,178 B1 * 11/2001 Hale et al. ...................... 514/2.3

FOREIGN PATENT DOCUMENTS

WO   WO 03101283 A2 * 12/2003

OTHER PUBLICATIONS

Moore, S., et al., Aug. 21, 2007, Accession No. A6QLX3, Database Uniprot in GenCore version 6.3, Bioccelaration Ltd.*
Copeland, A., et al, Oct. 31, 2006, Accession No. Q07KC9, Database Uniprot in GenCore version 6.3, Bioccelartion Ltd.*
PCT/US06/13476 International Search Report and Written Opinion dated Oct. 18, 2006.
Fosbrink et al, "Overexpression of RGC-32 in Colin Cancer and Other Tumors," Experimental and Molecular Pathology 78(2005) p. 116-122.
Badea et al, "RGC-32 Increases $p34^{cdc2}$ Kinase Activity and Entry of Aortic Smooth Muscle Cells into S-phase," The Journal of biological Chemistyr, vol. 277, No. 1, Issue of Jan. 4, pp. 502-508, 2002.
Galfre, G. and Milstein, C., "Preparation of Monoclonal Antibodies: Strategies and Procedures," Methods in Enzymology, vol. 73, Academic Press, Inc., 1981.
Gossow, D. and Seemann, G., "Humanization of Monoclonal Antibodies," Methods in Enzymology, vol. 203, Academic Press, Inc., 1991.

* cited by examiner

*Primary Examiner* — Alana Harris Dent
*Assistant Examiner* — Anne Holleran
(74) *Attorney, Agent, or Firm* — Roylance, Abrams, Berdo & Goodman, L.L.P.

(57) ABSTRACT

The invention relates to antibodies that bind to a fragment of the Response Gene to Complement-32 (RGC-32), as well as methods of using these antibodies. Particular methods of using the antibodies of the present invention include, but are not limited to, methods of detecting RGC-32 in a sample, methods of assaying cell proliferation, as well as methods of detecting and/or monitoring the progression of abnormal conditions in a subject, where the disease states are associated with the presence or absence of RGC-32.

13 Claims, 11 Drawing Sheets

Human RGC-32 DNA sequence

```
  1 gcggccgcgt cgaccgggcg gcaagccccc gaatagcccc ggctgccacc tcgcaggacc caaggccacg
 61 gtgcgggaca gcaagcccgc ggctggagcg cagcgccgaa gggactggca gggctgaagt
121 cgcgccgggc ccagctgagc cgcctcatga cgcctgagct ggcctggact ctggccgact cggcgtcgcc cttccacgag cgccacttcc
181 tgtgcgagtt tgacgcggtg gcacctggag gcatcgaagc cgtcgtgcc ggccagtgtc agcgacagca
241 actacgagga gcacctggag gcacctggag cgactcggag agtgcagatt cactttatag gaacagcttc agcttcagtg
301 gcggcttcag cgactcggag agtgcagatt cactttatag gaacagcttc agcttcagtg
361 atgaaaact gaattctcca acagactcta ccccagctct tctctctgcc actgtcactc
421 ctcagaaagc taaattagga gacacaaaag agctagaaag cttcattgct gatccttgaca
481 aaactttagc aagtatgtga aacaagaagt tctggtcct ttcatcataa gggagaagct
541 tcagaaagtt ccgaggacct tcaacctttct gctactagaa tctgctgcca cagcccttga
601 agacgtgcac tcaacctttct accaggccac tctcaggctc ctgactttgt ttacctgctt gcagcatatt
661 tcccatttct gggcaattta gacagtgaaa ctgactttgt ttctcttaaa acatagcttt cctgtaattt
721 agaacagacg atccatgcta atattgtatt ttctcttaaa acatagcttt cctgtaattt
781 aaagtgcttt tatgaaaata tttgtaatta attatatata gttgaaaata gcagtaagct
841 ttcccattat aatatatttt tgtatacaaa taaaatttga actgaacctc gtgcc (SEQ ID NO:3)
```

1 MKPPAEDLSD ALCEFDAVLA DFASPFHERH FHYEEHLERM KRRSSASVSD SSGFSDSESA
 61 DSLYRNSFSF SDEKLNSPTD STPALLSATV TPQKAKLGDT KELEAFIADL DKTLASM (SEQ ID NO:2)

1 ASPFHERHFH (SEQ ID NO:1)

FIGURE 9

SEQUENCE LISTING

<160> NUMBER OF SEQ ID NOS: 5

<210> SEQ ID NO 1
<211> LENGTH: 10
<212> TYPE: PRT
<213> ORGANISM: Homo sapiens

<400> SEQUENCE: 1

Ala Ser Pro Phe His Glu Arg His Phe His
 1               5                  10

<210> SEQ ID NO 2
<211> LENGTH: 117
<212> TYPE: PRT
<213> ORGANISM: Homo sapiens

<400> SEQUENCE: 2

Met Lys Pro Pro Ala Glu Asp Leu Ser Asp Ala Leu Cys Glu Phe Asp
 1               5                  10                  15

Ala Val Leu Ala Asp Phe Ala Ser Pro Phe His Glu Arg His Phe His
                20                  25                  30

Tyr Glu Glu His Leu Glu Arg Met Lys Arg Arg Ser Ser Ala Ser Val
            35                  40                  45

Ser Asp Ser Ser Gly Phe Ser Asp Ser Glu Ser Ala Asp Ser Leu Tyr
 50                  55                  60

Arg Asn Ser Phe Ser Phe Ser Asp Glu Lys Leu Asn Ser Pro Thr Asp
 65                  70                  75                  80

Ser Thr Pro Ala Leu Leu Ser Ala Thr Val Thr Pro Gln Lys Ala Lys
                85                  90                  95

Leu Gly Asp Thr Lys Glu Leu Glu Ala Phe Ile Ala Asp Leu Asp Lys
            100                 105                 110

Thr Leu Ala Ser Met
        115

<210> SEQ ID NO 3
<211> LENGTH: 895
<212> TYPE: DNA
<213> ORGANISM: Homo sapiens

<400> SEQUENCE: 3
gcggccgcgt cgaccggcgc ggctggagcg cagcgccgaa gggactggca gggctgaagt      60
gtgcgggaca gcaagccccc gaatagcccc ggctgccacc tcgcaggacc caaggccacg     120
cgcgccgggc ccagctgagc cgcctcatga agccgcccgc ggaggacctg tcggacgcgc     180
tgtgcgagtt tgacgcggtg ctggccgact tcgcgtcgcc cttccacgag cgccacttcc     240
actacgagga gcacctggag cgcatgaagc ggcgcagcag cgccagtgtc agcgacagca     300
gcggcttcag cgactcggag agtgcagatt cactttatag gaacagcttc agcttcagtg     360
atgaaaaact gaattctcca acagactcta ccccagctct tctctctgcc actgtcactc     420
ctcagaaagc taaattagga gacacaaaag agctagaagc cttcattgct gatcttgaca     480 aactttagc aagtatgtga acaagaagt tctgggtcct ttcatcataa gggagaagct     540
tcagaaagtt ccgaggacct gctaaaatca gctactagaa tctgctgcca gaggggacaa     600
agacgtgcac tcaaccttct accaggccac tctcaggctc accttaaaat cagcccttga     660
tcccatttct gggcaattta gacagtgaaa ctgactttgt ttacctgctt gcagcatatt     720
agaacagacg atccatgcta atattgtatt ttctcttaaa acatagcttt cctgtaattt     780

```
aaagtgcttt tatgaaaata tttgtaatta attatatata gttggaaata gcagtaagct    840
ttcccattat aatatatttt tgtatacaaa taaaatttga actgaacctc gtgcc         895

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gccacttcca ctacgaggag                                                 20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtggcctggt agaaggttga                                                 20
```

MONOCLONAL ANTIBODIES WITH BINDING SPECIFICITY FOR RESPONSE GENE TO COMPLEMENT 32 (RGC-32)

RELATED APPLICATIONS

This application is a national stage application, filed under 35 U.S.C. §371, of International Application No. PCT/US2006/013476 filed Apr. 10, 2006, which claims priority to U.S. Provisional Application No. 60/669,463 filed Apr. 8, 2005, the contents of which are incorporated by reference.

STATEMENT REGARDING FEDERALLY SPONSORED RESEARCH OR DEVELOPMENT

This invention was made with government support under Grant Number NS042011 awarded by the National Institutes of Health and with government support from the US Department of Veterans Affairs. The government has certain rights in the invention.

BACKGROUND OF THE INVENTION

1. Field of the Invention

The invention relates to antibodies that bind to a fragment of the Response Gene to Complement-32 (RGC-32), as well as methods of using these antibodies.

2. Background of the Invention

Progression through each phase of the cell cycle is controlled by specific cyclin dependent kinases (CDK) and their interactions with cyclins and CDK inhibitors (CKI). The expression of each cyclin fluctuates throughout the cell cycle, and CKI are down-regulated in response to mitogenic stimulation (Sherr C. J. *Science*, 274:1672-1677 (1996), which is incorporated by reference). CDK are a family of serine/threonine protein kinases that are regulated by multiple mechanisms leading to their activation at specific points of the cell cycle. Mitosis is regulated by CDC2 when in complex with cyclin B (Nigg, E. A., *Nat. Rev. Mol. Cell. Biol.*, 2, 21-32 (2001), incorporated by reference). Deregulation of the cell cycle is well documented in cancer (See Sherr, C. J., *Cancer Res.*, 60, 3689-3695 (2000), which is incorporated by reference), and compounds with CDK inhibitory activity have recently entered clinical trials (See Vermeulen, K., et al., Cell Prolif. 36: 131-149 (2003), which is incorporated by reference). The expression of CDC2, CDK2 and CDK4 proteins is higher in colon cancer cells than in normal mucosa (See Kim, J. H. et al., *Cancer*, 85: 546-553 (1999) and Salh, B., et al., *Anticancer Res.*, 19:741-748 (1999), which are incorporated by reference.) Higher levels of cyclins D1, D3, A and E were also found in primary colorectal carcinomas than in the adjacent normal areas (See Arber, N., et al., *Gastroenterology*, 110: 669-674 (1996), Handa, K., et al., *Int J Cancer*, 84: 225-233 (1999) and Sutter, T., et al., *J Med*, 28: 285-309 (1997), all of which are incorporated by reference). CDC2 kinase activity is also documented to be increased in colon cancer tissue, but not in normal tissue. CDC2 is mostly present in colon cancer cells positive for phosphorylated Rb protein (Yamamoto, H., et al., *Br. J. Cancer.*, 71: 1231-1236 (1995), which is incorporated by reference), and its overexpression is higher in focal carcinomas (Yamamoto, H., et al., *Int J Oncol*, 13: 233-239 (1998), which is incorporated by reference). The cyclin dependent pathway is, however, complicated and other factors are necessary for proper function and progression through the cell cycle.

One of these other factor, the Response Gene to Complement (RGC)-32 was first cloned in the rat by differential display (See Badea, T. et al., *J. Biol. Chem.*, 273:266977-26981 (1998), which is incorporated by reference), and subsequently from human brain library (See Badea, T. et al., *J. Biol. Chem.* 277:502-508 (2005), which is incorporated by reference). Overexpression of RGC-32 is associated with an increase in DNA synthesis, thus leading to the hypothesis that RGC-32 is involved in activation of the cell cycle Badea, T. et al., *J. Biol. Chem.*, 273:266977-26981 (1998). Experimental evidence indicates that RGC-32 has an important role in cell cycle activation through regulation of CDC2 kinase (Badea, T. et al., *J. Biol. Chem.* 277:502-508 (2005)). Overexpression of RGC-32 in human aortic smooth muscle cells (SMC) increased BrdU incorporation and the number of cells progressing into G2/M phase. RGC-32 appears to complex with CDC2/cyclin B1 and increase the kinase activity of CDC2. This kinase-enhancing activity requires CDC2 phosphorylation of RGC-32 at Threonine 91. These findings identify RGC-32 as a substrate and regulator of CDC2.

The present invention exploits the surprising discovery that RGC-32 mRNA and protein are expressed in colon carcinoma and other types of cancer, although it does not appear to be expressed at the protein level in normal, surrounding tissue. Indeed, both mRNA levels and protein levels of RGC-32 are increased in tumor tissues. Specifically, immunohistochemistry analysis revealed that RGC-32 is localized in the malignant epithelial cells, but not in adjacent non-neoplastic colonic epithelium, in colon carcinoma. RGC-32 protein was overexpressed in tumor cells that also showed the presence of proliferation marker Ki-67. As a result, increased expression of RGC-32 may be part of the deregulation of the cell cycle that is required for aberrant cell division, neoplastic growth, T-cell proliferation and/or tumor growth and may be useful as a method of detecting various abnormalities.

SUMMARY OF THE INVENTION

The present invention relates to antibodies that bind to an antigen, where the antigen comprises an amino acid sequence at least 80% identical to the amino acid sequence of SEQ ID NO:1.

The present invention also relates to methods of detecting an antigen in a biological sample, where the antigen comprises an amino acid sequence at least 80% identical to the amino acid sequence of SEQ ID NO:1.

The present invention also relates to methods of detecting an abnormal condition is a subject. These methods comprise determining the levels of an antigen in a sample, where the antigen comprises an amino acid sequence at least 80% identical to the amino acid sequence of SEQ ID NO:1 and comparing these levels to normal levels of the antigen. An abnormal condition may be indicated by a difference in the measured levels of the antigen and normal levels.

The present invention also relates to methods of monitoring the progression of an abnormal condition in a subject. These methods comprise determining the levels of an antigen in a sample at two more time points, where the antigen comprises an amino acid sequence at least 80% to the amino acid sequence. The measured levels at each of the time points are compared to one another to determine a difference in level on antigen over time. Progression, regression or stasis of the abnormal condition may be indicated by a difference in the measured levels of the antigen in the subject over time.

BRIEF DESCRIPTION OF THE DRAWINGS

FIG. 9 depicts the DNA sequence human RGC-32 (A) (as reported in J. Biol. Chem. 2002, 277, 502-508) and the portions used to generate the antibodies of the present invention. (B) An amino acid sequence (SEQ ID NO:2) of a fragment of human RGC-32 protein. (C) The 10 amino acid fragment (SEQ ID NO:1) that was used to generate the novel antibodies of the present invention.

DETAILED DESCRIPTION OF THE INVENTION

Figure 1A:
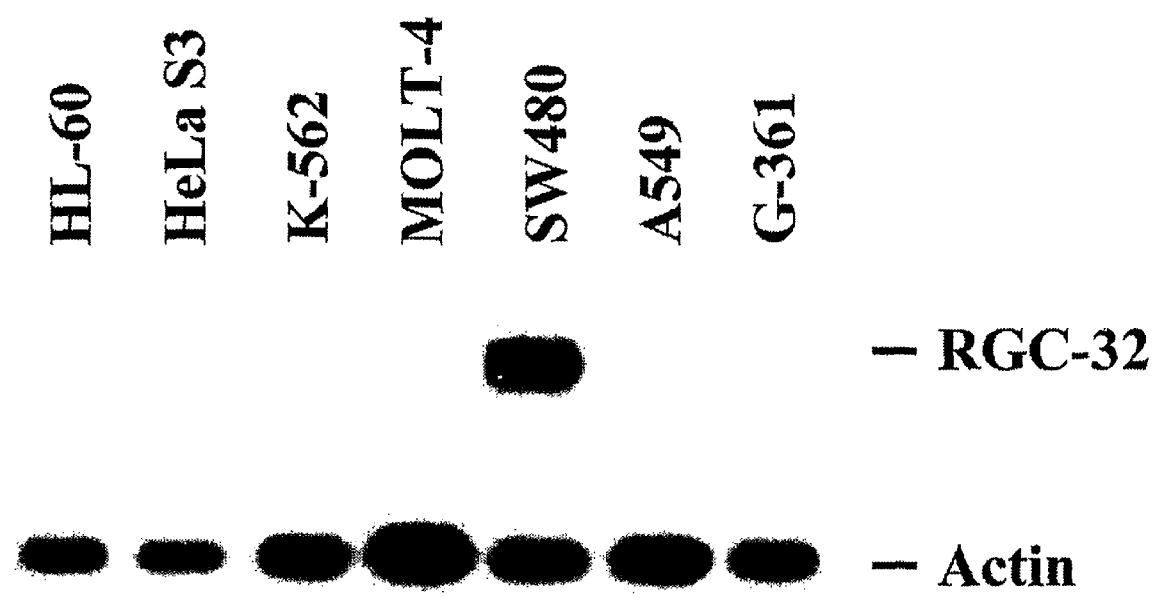
FIG. 1 depicts a Northern blot for RGC-32 in cancerous cells and tissue. (A) A Northern blot of cancer cells. A Northern blot (Human Cancer Cell Line MTN Blot II from Clontech) that contains 2 µg of poly A+ RNA from various cancer cell lines was hybridized with $^{32}$[P]-labeled RGC-32 or β-actin cDNA probe. After extensive washing, the blot was autoradiographed. β-Actin was used as loading control. The colon adenocarcinoma cell line (SW480) exhibited the highest level of expression. (B) Northern blot of tumor tissues. A Northern blot (Human Tumor MTN Blot from Clontech) that contains 10 µg of total RNA from various human cancer tissues was hybridized with $^{32}$[P]-labeled RGC-32 or β-actin cDNA probes. Lung, stomach and colon tumor tissues, exhibited the highest levels of expression for RGC-32, while ovary, uterus and rectum showed moderate to low levels of RGC-32 expression.

The present invention relates to antibodies that bind to an antigen, where the antigen comprises an amino acid sequence at least 80% identical to the amino acid sequence of SEQ ID NO:1.

As used herein, the term "antibody" is used to mean immunoglobulin molecules and functional fragments thereof, regardless of the source or method of producing the fragment. As used herein, a "functional fragment" of an immunoglobulin is a portion of the immunoglobulin molecule that specifically binds to a binding target. Thus, the term "antibody" as used herein encompasses whole antibodies, such as antibodies with isotypes that include but are not limited to IgG, IgM, IgA, IgD, IgE and IgY, and even single-chain antibodies found in some animals e.g., camels, as well as fragments that specifically bind to target. Whole antibodies or fragments thereof may be monoclonal or polyclonal, and they may be humanized or chimeric. The term "monoclonal antibody" as used herein is not limited to antibodies produced through hybridoma technology. Rather, the term "monoclonal antibody" refers to an antibody that is derived from a single clone, including any eukaryotic, prokaryotic, or phage clone, and not the method by which it is produced. The term "antibody" also encompasses functional fragments of immunoglobulins, including but not limited to Fab fragments, Fab' fragments, F(ab')$_2$ fragments and Fd fragments. "Antibody" also encompasses fragments of immunoglobulins that comprise at least a portion of a $V_L$ and/or $V_H$ domain, such as single chain antibodies, a single-chain Fv (scFv), disulfide-linked Fvs and the like.

The antibodies used in the present invention may be monospecific, bispecific, trispecific or of even greater multispecificity. In addition the antibodies may be monovalent, bivalent, trivalent or of even greater multivalency. Furthermore, the antibodies of the invention may be from any animal origin including, but not limited to, birds and mammals. In specific embodiments, the antibodies are human, murine, rat, sheep, rabbit, goat, guinea pig, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described in U.S. Pat. No. 5,939,598, which is herein incorporated by reference.

The antibodies used in the present invention may be described or specified in terms of the epitope(s) or portion(s) of a polypeptide to which they recognize or specifically bind. Or the antibodies may be described based upon their ability to bind to specific conformations of the antigen, or specific modification (e.g., cleavage or chemical, natural or otherwise, modification of sequence).

The specificity of the antibodies used in present invention may also be described or specified in terms their binding affinity towards the antigen (epitope) or of by their cross-reactivity. Specific examples of binding affinities encompassed in the present invention include but are not limited to those with a dissociation constant (Kd) less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

The antibodies used in the invention also include derivatives that are modified, for example, by covalent attachment of any type of molecule to the antibody such that covalent attachment does not prevent the antibody from generating an anti-idiotypic response. Examples of modifications to antibodies include but are not limited to, glycosylation, acetylation, pegylation, phosphorylation, amidation, derivatization by known protecting/blocking groups, proteolytic cleavage, linkage to a cellular ligand or other composition, such as a signaling moiety, a label etc. In addition, the antibodies may be linked or attached to solid substrates, such as, but not limited to, beads, particles, glass surfaces, plastic surfaces, ceramic surfaces, metal surfaces. Any of numerous chemical modifications may be carried out by known techniques, including, but not limited to, specific chemical cleavage, acetylation, biotinylation, farnesylation, formylation, inhibition of glycosylation by tunicamycin and the like. Additionally, the derivative may contain one or more non-classical or synthetic amino acids.

The antibodies used in the present invention may be generated by any suitable method known in the art. Polyclonal antibodies can be produced by various procedures well known in the art. For example, the antigen or fragment thereof can be administered to various host animals including, but not limited to, rabbits, goats, chickens, mice, rats, to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (both of which are incorporated by reference).

Methods for producing and screening for specific antibodies using hybridoma technology are routine and well known in the art such as, but not limited to, immunizing a mouse, hamster, or rat. Additionally, newer methods to produce rabbit and other mammalian monoclonal antibodies may be available to produce and screen for antibodies. In short, methods of producing and screening antibodies, and the animals used therein, should not limit the scope of the invention. Once an immune response is detected, the mouse spleen is harvested and splenocytes isolated. The splenocytes are then fused by well known techniques to any suitable myeloma cells, for example cells from cell line SP2/0 available from the ATCC. Hybridomas are selected and cloned by limited dilution. The hybridoma clones can then be assayed by methods known in the art for cells that secrete antibodies capable of binding an antigen of the present invention. Ascites fluid, which generally contains high levels of antibodies, can be generated by immunizing mice with positive hybridoma clones. In addition, antibodies can be produced using a variety of alternate methods, including but not limited to bioreactors and standard tissue culture methods, to name a few.

The antibodies used the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library. Phage expressing an antigen binding domain that binds the antigen of interest can be selected or identified with the antigen of interest, such as using a labeled antigen or antigen bound or captured to a solid surface or bead. The phage used in these methods are typically filamentous phage including, but not limited to, fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187 9-18 (1997); Burton et al., *Advances in Immunology* 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108, all of which are incorporated by reference.

Antibody fragments which recognize specific epitopes may be generated by known techniques. For example, Fab and F(ab')$_2$ fragments of the invention may be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CH1 domain of the heavy chain.

Other methods, such as recombinant techniques, may be used to produce Fab, Fab' and F(ab')$_2$ fragments and are disclosed in PCT publication WO 92/22324; Mullinax et al., *BioTechniques* 12(6):864-869 (1992); and Sawai et al., *AJRI* 34:26-34 (1995); and Better et al., *Science* 240:1041-1043 (1988), which are herein incorporated by reference. After phage selection, for example, the antibody coding regions from the phage can be isolated and used to generate whole antibodies, including human antibodies, or any other desired antigen binding fragment, and expressed in any desired host, including mammalian cells, insect cells, plant cells, yeast, and bacteria.

Examples of techniques which can be used to produce other types of fragments, such as scFvs and include those described in U.S. Pat. Nos. 4,946,778 and 5,258,498; Huston et al., *Methods in Enzymology* 203:46-88 (1991); Shu et al., *Proc. Nat'l Acad. Sci.* (*USA*) 90:7995-7999 (1993); and Skerra et al., *Science* 240:1038-1040 (1988), all of which are incorporated by reference. For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, *Science* 229:1202 (1985); Oi et al., *BioTechniques* 4:214 (1986); Gillies et al., *J. Immunol. Methods* 125:191-202 (1989); U.S. Pat. Nos. 5,807,715; 4,816,567; and 4,816,397, all of which are herein incorporated by reference. Humanized antibodies are antibody molecules from non-human species antibody that bind the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See U.S. Pat. No. 5,585,089; Riechmann et al., *Nature* 332:323 (1988), both of which are herein incorporated by reference. Antibodies can be humanized using a variety of techniques known in the art including, for example, CDR-grafting (EP 239,400; PCT publication WO 91/09967; U.S. Pat. Nos. 5,225,539; 5,530, 101; and 5,585,089), veneering or resurfacing (EP 592,106; EP 519,596; Padlan, *Molecular Immunology* 28(4/5):489-498 (1991); Studnicka et al., *Protein Engineering* 7(6):805-814 (1994); Roguska. et al., *Proc. Nat'l. Acad. Sci.* 91:969-913 (1994)), and chain shuffling (U.S. Pat. No. 5,565,332), all of which are hereby incorporated by reference.

Completely human antibodies may be particularly desirable for therapeutic treatment or diagnosis of human patients. Human antibodies can be made by a variety of methods known in the art including phage display methods described above using antibody libraries derived from human immunoglobulin sequences. See also. U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated by reference.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, *Int. Rev. Immunol.* 13:65-93 (1995), which is hereby incorporated by reference. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference.

Still another approach for generating human antibodies utilizes a technique referred to as guided selection. In guided selection, a selected non-human monoclonal antibody, e.g., a mouse antibody, is used to guide the selection of a completely human antibody recognizing the same epitope. (Jespers et al., *Biotechnology* 12:899-903 (1988), herein incorporated by reference).

Various methods can be used to assess the functional activity of antibodies and fragments. For example, in one embodiment where one is assaying for the ability to bind or compete with a polypeptide for binding to, for example, RGC-32, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

The antibodies of the present invention must bind an antigen comprising a an amino acid sequence at least 80% identical to the amino acid sequence of SEQ ID NO:1. The terms "polypeptide" and "protein" are used interchangeably herein. And the terms "antigen" and "biomarker" are also used interchangeably, as they relate the antibodies and the methods of use described herein. In specific embodiments, the antigen is a polypeptide of comprising an amino acid sequence at least 80%, 85%, 90%, 95%, 97%, 98%, 99% or 100% identical to the amino acid sequence of SEQ ID NO:1. In another specific embodiment, the antigen comprises an amino acid sequence at least 80% identical to the amino acid sequence of SEQ ID NO:2. In even more specific embodiments, the antigen is a polypeptide of comprising an amino acid sequence at least 80%, 85%, 90%, 95%, 97%, 98%, 99% or 100% identical to the amino acid sequence of SEQ ID NO:2.

As used herein, "identity" as it relates to amino acid sequence or polynucleotide sequences is a measure of the identity of nucleotide sequences or amino acid sequences compared to a reference nucleotide or amino acid sequence, usually a wild-type sequence. In general, the sequences are aligned so that the highest order match is obtained. "Identity" per se has an art-recognized meaning and can be calculated using published techniques. (See, e.g., Computational Molecular Biology, Lesk, A. M., ed., Oxford University Press, New York (1988); Biocomputing: Informatics And Genome Projects, Smith, D. W., ed., Academic Press, New York (1993); Computer Analysis of Sequence Data, Part I, Griffin, A. M., and Griffin, H. G., eds., Humana Press, New Jersey (1994); von Heinje, G., Sequence Analysis In Molecular Biology, Academic Press (1987); and Sequence Analysis Primer, Gribskov, M. and Devereux, J., eds., M Stockton Press, New York (1991)). While several methods exist to measure identity between two polynucleotide or polypeptide sequences, the term "identity" is well known in the art (Carillo, H. & Lipton, D., Siam J Applied Math 48:1073 (1988)). Methods commonly employed to determine identity or similarity between two sequences include, but are not limited to, those disclosed in Guide to Huge Computers, Martin J. Bishop, ed., Academic Press, San Diego (1994) and Carillo, H. & Lipton, D., Siam J Applied Math 48:1073 (1988). Computer programs may also contain methods and algorithms that calculate identity and similarity. Examples of computer program methods to determine identity and similarity between two sequences include, but are not limited to, GCS program package (Devereux, J., et al., Nucleic Acids Research 12(i): 387 (1984)), BLASTP, BLASTN, FASTA (Atschul, S. F., et al., J Molec Biol 215:403 (1990)).

A polypeptide having an amino acid sequence at least, for example, about 95% "identical" to a reference nucleotide sequence encoding a peptide of interest, for example RGC-32 or an antibody to RGC-32, is understood to mean that the amino acid sequence of the peptide is identical to the reference sequence except that the amino acid sequence may include up to about five mutations per each 100 amino acids of the reference peptide sequence encoding the anti-RGC-32 peptide being used as the reference sequence. In other words, to obtain a polypeptide having an amino acid sequence at least about 95% identical to a reference amino acid sequence, up to about 5% of the amino acids in the reference sequence may be deleted or substituted with another amino acid, or a number of amino acids up to about 5% of the total amino acids in the reference sequence may be inserted into the reference sequence. These mutations of the reference sequence may occur at the N- or C-terminal positions of the reference amino acid sequence or anywhere between those terminal positions, interspersed either individually among amino acids in the reference sequence or in one or more contiguous groups within the reference sequence.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and the DNA sequence encoding the polypeptide, to obtain a polypeptide with similar, if not identical, properties. It is thus contemplated by the inventors that various changes may be made in the peptide sequences of the disclosed compositions.

In making such changes, the hydropathic index of amino acids may or may not be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn may define the interaction of the protein with other molecules, for example, enzymes, substrates, receptors, DNA, antibodies, antigens, and the like.

Each naturally occurring amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (4.5). Of course, non-naturally occurring amino acids, which have their own hydrophobicity and charge characteristics may be used in the present invention.

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices may be within ±0.2 units in the hydropathic index. In one particular embodiment, amino acids are substituted with alternate amino acids that are within ±0.1 units in the hyphopathic index. In a more particular embodiment, amino acids are substituted with alternate amino acids that are within ±0.05 units in the hyphopathic index.

It is also understood in the art that the substitution of like amino acids can be made effectively on the basis of hydrophilicity. As detailed in U.S. Pat. No. 4,554,101, incorporated by reference, the following hydrophilicity values have been assigned to amino acid residues: arginine (+3.0); lysine (+3.0); aspartate (+3.0±0.1); glutamate (+3.0±0.1); serine (+0.3); asparagine (+0.2); glutamine (+0.2); glycine (0); threonine (−0.4); proline (−0.5±0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent protein. In making such changes, the substitution of amino acids whose hydrophilicity indices may be within ±0.2 units in the hydrophilicty index. In one particular embodiment, amino acids are substituted with alternate amino acids that are within ±0.1 units in the hydrophilicity index. In a more particular embodiment, amino acids are substituted with alternate amino acids that are within ±0.05 units in the hydrophilicity index.

As outlined above, amino acid substitutions are generally therefore based on the relative similarity of the amino acid side-chain substituents, for example, their hydrophobicity, hydrophilicity, charge, size, and the like. Exemplary substitutions which take variations of the foregoing characteristics into consideration are well known to those of skill in the art and include: arginine and lysine; glutamate and aspartate; serine and threonine; glutamine and asparagine; and valine, leucine and isoleucine.

As used herein, "isolated" as it relates to a polypeptide or nucleic acid molecule, is used to mean a polypeptide or nucleic acid molecule that has been removed from its native environment. For example, polypeptides that have been removed or purified from cells are considered isolated. In addition, recombinantly produced polypeptides molecules contained in host cells are considered isolated for the purposes of the present invention. Similarly, recombinant DNA molecules contained in a vector are considered isolated for the purposes of the present invention. Further examples of isolated DNA molecules include, but are not limited to, recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

The present invention also relates to nucleic acids encoding the antibodies of the present invention.

Nucleic acid molecules of the present invention may be in the form of RNA, such as but not limited to mRNA, or in the form of DNA, including, for instance, cDNA and genomic DNA obtained by cloning or produced synthetically. The DNA may be, but is not limited to, double-stranded or single-stranded. Single-stranded DNA or RNA may be the coding strand, also known as the sense strand, or it may be the non-coding strand, also referred to as the anti-sense strand.

Using the information provided herein, a nucleic acid molecule of the present invention encoding an antibody specific for, e.g., the RGC-32 biomarker may be obtained using standard cloning and screening procedures, such as those for cloning cDNAs using mRNA as starting material.

Nucleotide sequences can be determined using an automated DNA sequencer (such as the Model 373 from Applied Biosystems, Inc.). Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding an antibody to, for example, RGC-32. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule or polypeptide is at least 80%, 85%, 90%, 92%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. 6:237-245 (1990)). In a sequence alignment the query and subject sequences are both DNA sequences. An RNA sequence can be compared by converting U's to T's. The result of said global sequence alignment is in percent identity. Parameters that may be used in a FASTDB alignment of DNA sequences to calculate percent identity include, but are not limited to: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction can be made because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Nucleotide matching/alignment is determined by results of the FASTDB sequence alignment. The alignment percentage is then subtracted from the percent identity, calculated by the above FASTDB program using the specified parameters, to arrive at a final percent identity score. This corrected score can be used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. In this example, the deletions occur at the 5' end of the subject sequence and therefore, the FASTDB alignment does not show a match/alignment of the first 10 bases at the 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected.

Of course, due to the degeneracy of the genetic code, one of ordinary skill in the art will immediately recognize that a large number of the nucleic acid molecules having a sequence at least 80%, 85%, 90%, 92%, 95%, 96%, 97%, 98% or 99% identical to the reference nucleic acid can encode a polypeptide that may bind an antigen, e.g., RGC-32. In fact, since degenerate variants of these nucleotide sequences all encode the same polypeptide, this will be clear to the skilled artisan even without performing the above described comparison assay.

The present invention is further directed to polynucleotides comprising, or alternatively consisting of, isolated nucleic acid molecules which encode domains of domains of the antibodies of the present invention.

In another aspect, the invention provides an isolated nucleic acid molecule comprising, or alternatively consisting of, a polynucleotide which hybridizes under stringent hybridization conditions to a portion of the polynucleotide in a nucleic acid molecule of the invention described above. By "stringent hybridization conditions" is intended overnight incubation at 42° C. in a solution comprising, or alternatively consisting of 50% formamide, 5×SSC (750 mM NaCl, 75 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more in particular at least about 20 nt, still more particular at least about 30 nt, and even more particular about 30-70 nt of the reference polynucleotide. In this context "about" includes the particularly recited value and values larger or smaller by several (5, 4, 3, 2, or 1) nucleotides. These polynucleotides may be useful as diagnostic probes and primers. By a portion of a polynucleotide of "at least 20 nt in length," for example, is intended 20 or more contiguous nucleotides from the nucleotide sequence of the reference polynucleotide.

Of course, a polynucleotide which hybridizes only to a poly A sequence or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (i.e., practically any double-stranded cDNA generated from an oligo-dT primed cDNA library).

As indicated, nucleic acid molecules of the present invention which encode an antibody of the present invention may include, but are not limited to those encoding the amino acid sequence of the polypeptide, by itself; the coding sequence for the polypeptide and additional sequences, such as those encoding a leader or secretory sequence, such as a pre-, or pro- or prepro-protein sequence; the coding sequence of the polypeptide, with or without the aforementioned additional coding sequences, together with additional, non-coding sequences, including, for example, but not limited to introns and non-coding 5' and 3' sequences, such as the transcribed, non-translated sequences that play a role in transcription, mRNA processing, including splicing and polyadenylation signals, e.g., ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821-824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37:767 (1984).

A preferred fusion protein comprises a heterologous region from immunoglobulin that is useful to solubilize proteins. For example, fusion proteins comprising various portions of constant region of immunoglobin molecules together with another human protein or part thereof are well known in the art. In many cases, the Fc portion of the fusion protein is thoroughly advantageous for use in therapy and diagnosis and thus results, for example, in improved pharmacokinetic properties. On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL-5-receptor has been fused with Fc portions for the purpose of high-throughput screening assays to identify antagonists of hIL-5. See, D. Bennett et al., *Journal of Molecular Recognition*, Vol. 8:52-58 (1995) and K. Johanson et al., *The Journal of Biological Chemistry*, Vol. 270, No. 16:9459-9471 (1995).

The present invention further relates to variants of the nucleic acid molecules of the present invention, which encode portions, analogs or derivatives of the antibodies of the present invention. Variants may occur naturally, such as a natural allelic variant. By an "allelic variant" is intended one of several alternate forms of a gene occupying a given locus on a chromosome of an organism.

Non-naturally occurring variants may be produced using art-known mutagenesis techniques, which include, but are not limited to: oligonucleotide mediated mutagenesis, alanine scanning, PCR mutagenesis, site-directed mutagenesis (see, e.g., Carter et al., *Nucl. Acids Res.* 13:4331 (1986); and Zoller et al., *Nucl. Acids Res.* 10:6487 (1982)), cassette mutagenesis (see, e.g., Wells et al., *Gene* 34:315 (1985)), restriction selection mutagenesis (see, e.g., Wells et al., *Philos. Trans. R. Soc. London Ser. A* 317:415 (1986)).

Such variants include those produced by nucleotide substitutions, deletions or additions which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the antibodies. Also especially preferred in this regard are conservative substitutions.

The present invention also relates to vectors which include the isolated DNA molecules of the present invention, host cells which are genetically engineered with the recombinant vectors, and the production of antibodies or fragments thereof by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors may include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli*, *Streptomyces* and *Salmonella typhimurium* cells; fungal cells, such as yeast cells; insect cells such as *Drosophila* S2 and *Spodoptera* SD cells; animal cells such as CHO, COS and Bowes melanoma cells; and plant cells. Appropriate culture mediums and conditions for the above-described host cells are known in the art.

In addition to the use of expression vectors in the practice of the present invention, the present invention further includes novel expression vectors comprising operator and promoter elements operatively linked to nucleotide sequences encoding a protein of interest.

One example of such a vector is pHE4 which is described in detail below. Components of the pHE4-5 vector include: 1) a neomycinphosphotransferase gene as a selection marker, 2) an *E. coli* origin of replication, 3) a T5 phage promoter sequence, 4) two lac operator sequences, 5) a Shine-Delgarno sequence, 6) the lactose operon repressor gene (lacIq). The origin of replication (oriC) is derived from pUC19 (Invitrogen, Carlsbad, Calif.). The promoter sequence and operator sequences were made synthetically. Synthetic production of nucleic acid sequences is well known in the art. A nucleotide sequence encoding an antibody of the present invention is, for example, operatively linked to the promoter and operator by inserting the nucleotide sequence between the two restriction sites the pHE4 vector.

As noted above, the pHE4 vector contains a lacIq gene. LacIq is an allele of the lad gene which confers tight regulation of the lac operator. The lacIq gene encodes a repressor protein which binds to lac operator sequences and blocks transcription of down-stream (i.e., 3') sequences. The lacIq gene product, however, dissociates from the lac operator in the presence of either lactose or certain lactose analogs, e.g., isopropyl B-D-thiogalactopyranoside (IPTG). The antibody would thus not be produced in appreciable quantities in uninduced host cells containing the pHE4 vector. Induction of these host cells by the addition of an agent such as IPTG, however, would result in the expression of the antibody coding sequence.

The promoter/operator sequences of the pHE4 vector comprise a T5 phage promoter and two lac operator sequences. One operator is located 5' to the transcriptional start site and the other is located 3' to the same site. These operators, when present in combination with the lacIq gene product, confer tight repression of down-stream sequences in the absence of a lac operon inducer, e.g., IPTG. Expression of operatively linked sequences located down-stream from the lac operators may be induced by the addition of a lac operon inducer, such as IPTG. Binding of a lac inducer to the lacIq proteins results in their release from the lac operator sequences and the initiation of transcription of operatively linked sequences. Lac operon regulation of gene expression is reviewed in Devlin, T., Textbook of Biochemistry with Clinical Correlations, 4th Edition (1997), pages 802-807.

Among known bacterial promoters suitable for use in the production of proteins of the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metallothionein-I promoter.

The pHE4 vectors also contains a Shine-Delgarno sequence 5' to the AUG initiation codon. Shine-Delgarno sequences are short sequences generally located about 10 nucleotides up-stream (i.e., 5') from the AUG initiation codon. These sequences essentially direct prokaryotic ribosomes to the AUG initiation codon.

Among vectors for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology (1986).

The polypeptides may be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In one embodiment, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

The present invention also relates to methods of detecting an antigen in a biological sample, where the antigen comprises an amino acid sequence at least 80% identical to the amino acid sequence of SEQ ID NO:1. Various methods can be used to detect the antigen in the sample, and can also be used to assess the functional activity of antibodies and fragments. For example, in one embodiment where one is assaying for the ability to bind or compete with a polypeptide for binding to, for example, RGC-32, various immunoassays known in the art can be used, including but not limited to, competitive and non-competitive assay systems using techniques such as a planar array, a radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. Specific embodiments of some of the assays listed include, but are not limited to, direct and indirect assays, as well as binary and tertiary sandwich assays. Other examples of assays that may be used in the methods of the present invention include, but are not limited to, bead or particle-based immunoassays, chemiluminescent assays, surface plasmon resonance (SPR) based assays, fluorescence assays, rolling-circle amplification assays, assays using dendrimers, and other enzyme or non-enzymatic amplification schemes.

The invention may also be used to screen antibodies that have been developed as potential therapeutics, such as, but not limited to, humanized antibodies. Vaccination studies may be undertaken that have the intent of generating antibodies in the subject that bind and antagonize the effects of the antigen of the present invention. The antibodies of the present invention may be used to compare the affinity or other characteristics of generated antibodies. Specifically, the invention provides methods of assessing the affinity of binding agents, e.g., antibodies or fragments thereof, comprising competition assays between the antibodies of the present invention and a different binding agent.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. In particular embodiments of the present invention, an antibody would be bound to a solid support (such as glass, polystyrene, polypropylene, polyethylene, dextran, nylon, amylases, natural and modified celluloses, polyacrylamides, agaroses, and magnetite). The nature of the carrier can be either soluble to some extent or insoluble for the purposes of the present invention. The support material may have virtually any possible structural configuration so long as the coupled molecule is capable of binding to the antigen. Thus, the support configuration may be spherical, as in a bead, or cylindrical, as in the inside surface of a test tube, or the external surface of a rod. Alternatively, the surface may be flat such as a sheet, test strip, etc. Those skilled in the art will note many other suitable carriers for binding antibody, or will be able to ascertain the same by use of routine experimentation.

For example, ELISA assays utilize a capture molecule that initially binds to the biomarker is or can be bound to the wells of culture plate. In this embodiment, the culture plate is acting as the carrier for the binding agent, i.e., the antibody. Subsequently, a labeled detection molecule (which may recognize the capture molecule or the biomarker) may be added to the test environment. One of skill in the art would be knowledgeable as to the parameters that can be modified to increase the signal detected as well as other variations of ELISAs known in the art. As used herein the term "capture molecule" is used mean a binding agent that immobilizes the antigen by its binding to the antigen. Further, an antigen is "immobilized" if the antigen or antigen-capture molecule complex is separated or is capable of being separated from the remainder of the sample. When the capture molecule is coated to a well or other surface, a detection molecule may be added following the addition of the antigen of interest to the wells. As used herein, a detection molecule is used to mean a molecule, such as an antibody or receptor, comprising a label. In a specific embodiment, the methods of the present invention comprise the use of a capturing antibody and a detection antibody to detect the antigen. In a more specific embodiment, the capture antibody and the detection antibody are the same antibodies with the same binding specificities. In another specific embodiment, the capture antibody and the detection antibody are different antibodies.

A label, as used herein, is intended to mean a chemical compound or ion that possesses or comes to possess or is capable of generating a detectable signal. The labels of the present invention may be conjugated to the primary binding agent, e.g., primary antibody, or secondary binding agent, e.g., secondary antibody, the antigen or a surface onto which the label and/or binding agent is attached. Examples of labels includes, but are not limited to, radiolabels, such as, for example, $^3$H and $^{32}$P, that can be measured with radiation-counting devices; pigments, biotin, dyes or other chromogens that can be visually observed or measured with a spectrophotometer; spin labels that can be measured with a spin label analyzer; and fluorescent labels (fluorophores), where the output signal is generated by the excitation of a suitable molecular adduct and that can be visualized by excitation with light that is absorbed by the dye or can be measured with standard fluorometers or imaging systems. Examples of suitable radioisotopic labels include $^{111}$In, $^{125}$I, $^{131}$I, $^{35}$S, $^{14}$C, $^{51}$Cr, $^{57}$Co, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd etc. Examples of suitable non-radioactive isotopic labels include $^{157}$Gd, $^{55}$Mn, $^{162}$Dy, $^{52}$Tr, $^{56}$Fe etc.

Additional examples of labels include, but are not limited to, a phosphorescent dye, a tandem dye and a particle. The label can be a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The term label also includes a "tag" or hapten that can bind selectively to a conjugated molecule such that the conjugated molecule, when added subsequently along with a substrate, is used to generate a detectable signal. For example, one can use biotin as a label and subsequently use an avidin or streptavidin conjugate of horseradish peroxidate (HRP) to bind to the biotin label, and then use a colorimetric substrate (e.g., tetramethylbenzidine (TMB)) or a fluorogenic substrate such as Amplex Red reagent (Molecular Probes, Inc.) to detect the presence of HRP. Numerous labels are know by those of skill in the art and include, but are not limited to, particles, fluorophores, haptens, enzymes and their colorimetric, fluorogenic and chemiluminescent substrates and other labels that are described in RICHARD P. HAUGLAND, MOLECULAR PROBES HANDBOOK OF FLUORESCENT PROBES AND RESEARCH PRODUCTS ($9^{th}$ edition, CD-ROM, (September 2002), which is herein incorporated by reference.

A fluorophore of the present invention is any chemical moiety that exhibits an absorption maximum beyond 280 nm, and when covalently attached to a labeling reagent retains its spectral properties. Fluorophores of the present invention include, without limitation; a pyrene (including any of the corresponding derivative compounds disclosed in U.S. Pat. No. 5,132,432, incorporated by reference), an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine (including any corresponding compounds in U.S. Ser. Nos. 09/968,401 and 09/969,853, incorporated by reference), a carbocyanine (including any corresponding compounds in U.S. Ser. Nos. 09/557,275; 09/969,853 and 09/968,401; U.S. Pat. Nos. 4,981,977; 5,268,486; 5,569,587; 5,569,766; 5,486,616; 5,627,027; 5,808,044; 5,877,310; 6,002,003; 6,004,536; 6,008,373; 6,043,025; 6,127,134; 6,130,094; 6,133,445; and publications WO 02/26891, WO 97/40104, WO 99/51702, WO 01/21624; EP 1 065 250 A1, incorporated by reference), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774,339; 5,187,288; 5,248,782; 5,274,113; and 5,433,896, incorporated by reference), a xanthene (including any corresponding compounds disclosed in U.S. Pat. Nos. 6,162,931; 6,130,101; 6,229,055; 6,339,392; 5,451,343 and U.S. Ser. No. 09/922,333, incorporated by reference), an oxazine (including any corresponding compounds disclosed in U.S. Pat. No. 4,714,763, incorporated by reference) or a benzoxazine, a carbazine (including any corresponding compounds disclosed in U.S. Pat. No. 4,810,636, incorporated by reference), a phenalenone, a coumarin (including an corresponding compounds disclosed in U.S. Pat. Nos. 5,696,157; 5,459,276; 5,501,980 and 5,830,912, incorporated by reference), a benzofuran (including an corresponding compounds disclosed in U.S. Pat. Nos. 4,603,209 and 4,849,362, incorporated by reference) and benzphenalenone (including any corresponding compounds disclosed in U.S. Pat. No. 4,812,409, incorporated by reference) and derivatives thereof. As used herein, oxazines include resorufins (including any corresponding compounds disclosed in U.S. Pat. No. 5,242,805, incorporated by reference), aminooxazinones, diaminooxazines, and their benzo-substituted analogs.

When the fluorophore is a xanthene, the fluorophore is optionally a fluorescein, a rhodol (including any corresponding compounds disclosed in U.S. Pat. Nos. 5,227,487 and 5,442,045, incorporated by reference), or a rhodamine (including any corresponding compounds in U.S. Pat. Nos. 5,798,276; 5,846,737; U.S. Ser. No. 09/129,015, incorporated by reference). As used herein, fluorescein includes benzo- or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945,171, incorporated by reference). Alternatively, the fluorophore is a xanthene that is bound via a linkage that is a single covalent bond at the 9-position of the xanthene. Preferred xanthenes include derivatives of 3H-xanthen-6-ol-3-one attached at the 9-position, derivatives of 6-amino-3H-xanthen-3-one attached at the 9-position, or derivatives of 6-amino-3H-xanthen-3-imine attached at the 9-position.

Fluorophores for use in the invention include, but are not limited to, xanthene (rhodol, rhodamine, fluorescein and derivatives thereof) coumarin, cyanine, pyrene, oxazine and borapolyazaindacene. Most preferred are sulfonated xanthenes, fluorinated xanthenes, sulfonated coumarins, fluorinated coumarins and sulfonated cyanines. The choice of the fluorophore attached to the labeling reagent will determine the absorption and fluorescence emission properties of the labeling reagent and immuno-labeled complex. Physical properties of a fluorophore label include spectral characteristics (absorption, emission and stokes shift), fluorescence intensity, lifetime, polarization and photo-bleaching rate all of which can be used to distinguish one fluorophore from another.

Typically the fluorophore contains one or more aromatic or heteroaromatic rings, that are optionally substituted one or more times by a variety of substituents, including without limitation, halogen, nitro, cyano, alkyl, perfluoroalkyl, alkoxy, alkenyl, alkynyl, cycloalkyl, arylalkyl, acyl, aryl or heteroaryl ring system, benzo, or other substituents typically present on fluorophores known in the art.

In one aspect of the invention, the fluorophore has an absorption maximum beyond 480 nm. In a particularly useful embodiment, the fluorophore absorbs at or near 488 nm to 514 nm (particularly suitable for excitation by the output of the argon-ion laser excitation source) or near 546 nm (particularly suitable for excitation by a mercury arc lamp).

Many of fluorophores can also function as chromophores and thus the described fluorophores are also preferred chromophores of the present invention.

In addition to fluorophores, enzymes also find use as labels. Enzymes are desirable labels because amplification of the detectable signal can be obtained resulting in increased assay sensitivity. The enzyme itself may not produce a detectable signal but is capable of generating a signal by, for example, converting a substrate to produce a detectable signal, such as a fluorescent, colorimetric or luminescent signal. Enzymes amplify the detectable signal because one enzyme on a labeling reagent can result in multiple substrates being converted to a detectable signal. This is advantageous where there is a low quantity of target present in the sample or a fluorophore does not exist that will give comparable or stronger signal than the enzyme. The enzyme substrate is selected to yield the preferred measurable product, e.g. colorimetric, fluorescent or chemiluminescence. Such substrates are extensively used in the art, many of which are described in the MOLECULAR PROBES HANDBOOK, supra.

In a specific embodiment, a colorimetric or fluorogenic substrate and enzyme combination uses oxidoreductases such as horseradish peroxidase and a substrate such as 3,3'-diaminobenzidine (DAB) and 3-amino-9-ethylcarbazole (AEC), which yield a distinguishing color (brown and red, respectively). Other colorimetric oxidoreductase substrates that yield detectable products include, but are not limited to: 2,2-azino-bis(3-ethylbenzothiazoline-6-sulfonic acid) (ABTS), o-phenylenediamine (OPD), 3,3',5,5'-tetramethylbenzidine (TMB), o-dianisidine, 5-aminosalicylic acid, 4-chloro-1-naphthol. Fluorogenic substrates include, but are not limited to, homovanillic acid or 4-hydroxy-3-methoxyphenylacetic acid, reduced phenoxazines and reduced benzothiazines, including Amplex® Red reagent and its variants (U.S. Pat. No. 4,384,042) and reduced dihydroxanthenes, including dihydrofluoresceins (U.S. Pat. No. 6,162,931, incorporated by reference) and dihydrorhodamines including dihydrorhodamine 123. Peroxidase substrates that are tyramides (U.S. Pat. Nos. 5,196,306; 5,583,001 and 5,731,158, incorporated by reference) represent a unique class of peroxidase substrates in that they can be intrinsically detectable before action of the enzyme but are "fixed in place" by the action of a peroxidase in the process described as tyramide signal amplification (TSA). These substrates are extensively utilized to label targets in samples that are cells, tissues or arrays for their subsequent detection by microscopy, flow cytometry, optical scanning and fluorometry.

Another preferred colorimetric (and in some cases fluorogenic) substrate and enzyme combination uses a phosphatase enzyme such as an acid phosphatase, an alkaline phosphatase or a recombinant version of such a phosphatase in combination with a colorimetric substrate such as 5-bromo-6-chloro-3-indolyl phosphate (BCIP), 6-chloro-3-indolyl phosphate, 5-bromo-6-chloro-3-indolyl phosphate, p-nitrophenyl phosphate, or o-nitrophenyl phosphate or with a fluorogenic substrate such as 4-methylumbelliferyl phosphate, 6,8-difluoro-7-hydroxy-4-methylcoumarinyl phosphate (DiFMUP, U.S. Pat. No. 5,830,912, incorporated by reference) fluorescein diphosphate, 3-O-methylfluorescein phosphate, resorufin phosphate, 9H-(1,3-dichloro-9,9-dimethylacridin-2-one-7-yl) phosphate (DDAO phosphate), or ELF 97, ELF 39 or related phosphates (U.S. Pat. Nos. 5,316,906 and 5,443,986, incorporated by reference).

Glycosidases, in particular beta-galactosidase, beta-glucuronidase and beta-glucosidase, are additional suitable enzymes. Appropriate colorimetric substrates include, but are not limited to, 5-bromo-4-chloro-3-indolyl beta-D-galactopyranoside (X-gal) and similar indolyl galactosides, glucosides, and glucuronides, o-nitrophenyl beta-D-galactopyranoside (ONPG) and p-nitrophenyl beta-D-galactopyranoside. Preferred fluorogenic substrates include resorufin beta-D-galactopyranoside, fluorescein digalactoside (FDG), fluorescein diglucuronide and their structural variants (U.S. Pat. Nos. 5,208,148; 5,242,805; 5,362,628; 5,576,424 and 5,773,236, incorporated by reference), 4-methylumbelliferyl beta-D-galactopyranoside, carboxyumbelliferyl beta-D-galactopyranoside and fluorinated coumarin beta-D-galactopyranosides (U.S. Pat. No. 5,830,912, incorporated by reference).

Additional enzymes include, but are not limited to, hydrolases such as cholinesterases and peptidases, oxidases such as glucose oxidase and cytochrome oxidases, and reductases for which suitable substrates are known.

Specific embodiments of the present invention comprise enzymes and their appropriate substrates to produce a chemiluminescent signal, such as, but not limited to, natural and recombinant forms of luciferases and aequorins. Chemiluminescence-producing substrates for phosphatases, glycosidases and oxidases such as those containing stable dioxetanes, luminol, isoluminol and acridinium esters are additionally useful.

Additional embodiments comprise haptens such as biotin. Biotin is useful because it can function in an enzyme system or fluorogenic system to further amplify the detectable signal, and it can function as a tag to be used in affinity chromatography for isolation purposes. For detection purposes, an enzyme conjugate that has affinity for biotin is used, such as avidin-HRP or streptavidin-HRP. Subsequently a peroxidase substrate is added to produce a detectable signal. Alternatively, a colorimetric or fluorimetric reporter dye or protein that has affinity for biotin is used, such as streptavidin-R-Phycoerythrin.

Haptens also include hormones, naturally occurring and synthetic drugs, pollutants, allergens, affector molecules, growth factors, chemokines, cytokines, lymphokines, amino acids, peptides, chemical intermediates, nucleotides and the like.

Fluorescent proteins also find use as labels for the labeling reagents of the present invention. Examples of fluorescent proteins include green fluorescent protein (GFP) and the phycobiliproteins and the derivatives thereof. The fluorescent proteins, especially phycobiliprotein, are particularly useful for creating tandem dye labeled labeling reagents. These tandem dyes comprise a fluorescent protein and a fluorophore for the purposes of obtaining a larger stokes shift wherein the emission spectra is farther shifted from the wavelength of the fluorescent protein's absorption spectra. This is particularly advantageous for detecting a low quantity of a target in a sample wherein the emitted fluorescent light is maximally optimized, in other words little to none of the emitted light is reabsorbed by the fluorescent protein. For this to work, the fluorescent protein and fluorophore function as an energy transfer pair wherein the fluorescent protein emits at the wavelength that the fluorophore absorbs at and the fluorophore then emits at a wavelength farther from the fluorescent proteins than could have been obtained with only the fluorescent protein. A particularly useful combination is the phycobiliproteins disclosed in U.S. Pat. Nos. 4,520,110; 4,859,582; 5,055,556, incorporated by reference, and the sulforhodamine fluorophores disclosed in U.S. Pat. No. 5,798,276, or the sulfonated cyanine fluorophores disclosed in U.S. Ser. Nos. 09/968/401 and 09/969/853, incorporated by reference; or the sulfonated xanthene derivatives disclosed in U.S. Pat. No. 6,130,101, incorporated by reference and those combinations disclosed in U.S. Pat. No. 4,542,104, incorporated by reference. Alternatively, the fluorophore functions as the energy donor and the fluorescent protein is the energy acceptor.

In one embodiment, the label is a fluorophore selected from the group consisting of fluorescein, coumarins, rhodamines, 5-TMRIA (tetramethylrhodamine-5-iodoacetamide), (9-(2 (or 4)-(N-(2-maleimdylethyl)-sulfonamidyl)-4(or 2)-sulfophenyl)-2,3,6,7,12,13,16,17-octahydro-(1H,5H,11H,15H-xantheno(2,3,4-ij:5,6,7-i'j')diquinolizin-18-ium salt) (Texas Red®), 2-(5-(1-(6-(N-(2-maleimdylethyl)-amino)-6-oxohexyl)-1,3-dihydro-3,3-dimethyl-5-sulfo-2H-indol-2-ylidene)-1,3-propyldienyl)-1-ethyl-3,3-dimethyl-5-sulfo-3H-indolium salt (Cy™3), N,N'-dimethyl-N-(iodoacetyl)-N'-(7-nitrobenz-2-oxa-1,3-diazol-4-yl)ethylenediamine (IANBD amide), 6-acryloyl-2-dimethylaminonaphthalene (acrylodan), pyrene, 6-amino-2,3-dihydro-2-(2-((iodoacetyl) amino)ethyl)-1,3-dioxo-1H-benz(de)isoquinoline-5,8-disulfonic acid salt (lucifer yellow), 2-(5-(1-(6-(N-(2-maleimdylethyl)-amino)-6-oxohexyl)-1,3-dihydro-3,3-dimethyl-5-sulfo-2H-indol-2-ylidene)-1,3-pentadienyl)-1-ethyl-3,3-dimethyl-5-sulfo-3H-indolium salt (Cy™5), 4-(5-(4-dimethylaminophenyl)oxazol-2-yl)phenyl-N-(2-bromoacetamidoethyl)sulfonamide (Dapoxyl® (2-bromoacetamidoethyl)sulfonamide)), (N-(4,4-difluoro-1,3,5,7-tetramethyl-4-bora-3a,4a-diaza-s-indacene-2-yl)iodoacetamide (BODIPY® 507/545 IA), N-(4,4-difluoro-5,7-diphenyl-4-bora-3a,4a-diaza-s-indacene-3-propionyl)-N'-iodoacetylethylenediamine (BODIPY 530/550 IA), 5-((((2-iodoacetyl)amino)ethyl) amino)naphthalene-1-sulfonic acid (1,5-IAEDANS), and carboxy-X-rhodamine, 5/6-iodoacetamide (XRIA 5,6). Another example of a label is BODIPY-FL-hydrazide. Other luminescent labels include lanthanides such as europium (Eu3+) and terbium (Tb3+), as well as metal-ligand complexes of ruthenium [Ru(II)], rhenium [Re(I)], or osmium [Os(II)], typically in complexes with diimine ligands such as phenanthroline.

The present invention also relates to methods of detecting an abnormal condition is a subject. These methods comprise determining the levels of an antigen in a sample, where the antigen comprises an amino acid sequence at least 80% to the amino acid sequence and comparing these levels to normal levels of the antigen. An abnormal condition may be indicated by a difference in the measured levels of the antigen and normal levels.

As used herein, an "abnormal condition" is used to mean a disease, or aberrant cellular or metabolic condition. Examples of abnormal conditions in which the methods can be used include but are not limited to, dysplasia, neoplastic growth and abnormal cell proliferation. In one embodiment, the abnormal condition comprises neoplastic growth. In a more specific embodiment, the abnormal condition comprises a carcinoma. In an even more specific embodiment, the abnormal condition comprises either squamous cell carcinoma or adenocarcinoma. The invention is not limited to the type of neoplasm, adenoma or carcinoma. For example, the adenoma or carcinoma may be a carcinoma of the digestive track or any associated glands or organs, including, but not limited to, the throat, the salivary glands, esophagus, the stomach, the small intestine, the large intestine, the pancreas. Additional forms of cancer include, but are not limited to, lung cancer, prostate cancer and breast cancer. Additional abnormal conditions include, but are not limited to, multiple sclerosis and other demyelinating diseases of the central nervous system (CNS), inflammatory CNS diseases (meningitis, meningoencephalitis) and degenerative disorders such as, but not limited to, Alzheimer's Disease and Parkinson disease.

The abnormal condition can also include other conditions or disorders that are marked by increased T-cell and/or macrophage activity such as atherosclerosis, inflammation and autoimmune diseases that include but are not limited to, rheumatoid arthritis, lupus, diabetes and Sjögren's syndrome. By "increased T-cell activity" or "increased macrophage activity" is meant the activation, differentiation, recruitment or proliferation of T-cells or macrophages. For example, "increased macrophage activity" can be marked by the presence macrophages, since macrophages differentiate from monocytes in response to pathogens or other antigenic sources. Similarly, "increased T-cell activity" can include, but is not limited to autocrine-induced proliferation, B-cell stimulation, T-cell migration and T-cell differentiation.

The levels of antigen of the subject may be assessed in vivo or in vitro, from a sample from the subject. As used herein, a sample can be any environment that may be suspected of containing the antigen of interest. Thus, a sample includes, but is not limited to, a solution, a cell or a portion thereof, tissue culture medium, a body fluid, a tissue or portion thereof, and an organ or portion thereof. Examples of cells include, but are not limited to, bacteria, yeast, plant, insect, avian, fish, reptilian, amphibian, and mammalian such as, for example, bovine, ovine, equine, porcine, canine, feline, human and nonhuman primates. Other examples include non-animal organisms that may harbor similar antigens of interest, include but are not limited to molds, viruses, and other model systems for the study of biological processes. The scope of the invention should not be limited by the cell type assayed or the media in which these cells are cultured or processed (e.g., for the production of cellular or tissue lysates). Examples of biological samples to be assayed include, but are not limited to, blood, plasma, serum, urine, saliva, milk, seminal plasma, synovial fluid, interstitial fluid, cerebrospinal fluid, lymphatic fluids, bile, and amniotic fluid, tissue culture medium, tissue homogenates, cell lysates, chemical solutions. In one embodiment, the sample is a serum sample taken from the subject. The scope of the methods of the present invention should not be limited by the type of sample assayed. The terms "subject" "patient" and "organism" are used interchangeably herein and are used to mean any animal. In one embodiment the animal is a mammal. In a more particular embodiment, the animal is a human or nonhuman primate.

The samples may or may not have been removed from their native environment. Thus, the portion of sample assayed need not be separated or removed from the rest of the sample or from a subject that may contain the sample. Of course, the sample may also be removed from its native environment. For example, the sample may be a tissue section or serum sample. Furthermore, the sample may be processed prior to being assayed. For example, the sample may be diluted or concentrated; the sample may be purified and/or at least one compound, such as an internal standard, may be added to the sample. The sample may also be physically altered (e.g., centrifugation, affinity separation) or chemically altered (e.g., adding an acid, base or buffer, heating) prior to or in conjunction with the methods of the current invention. Processing also includes freezing and/or preserving the sample prior to assaying.

The measurement of the levels of antigen may be qualitative or quantitative. For example, the levels of antigen may be quantified is some numerical expression, such as a ratio or a percentage.

Once the levels of antigen have been determined, this determination is then compared to normal levels of the antigen of the present invention. "Normal levels" of the antigen may be assessed by measuring levels of the antigen in a known healthy subject, including the same subject that is later screened or being diagnosed. Normal levels may also be assessed over a population sample, where a population sample is intended to mean either multiple samples from a single subject or at least one sample from a multitude of subjects. Normal levels of an antigen, in terms of a population of samples, may or may not be categorized according to characteristics of the population including, but not limited to, sex, age, weight, ethnicity, geographic location, fasting state, state of pregnancy or post-pregnancy, menstrual cycle, general health of the subject, alcohol or drug consumption, caffeine or nicotine intake and circadian rhythms.

A difference between normal levels and the measured levels of the antigen may indicate that the subject has a disease or abnormal condition or has a higher (or lower) probability of developing a disease or abnormal condition than normal subjects. In addition, the magnitude of difference between measured levels and normal levels of the antigen may also indicate the severity of disease or abnormal condition or the level of probability of developing a disease or abnormal condition, compared to normal subjects.

The difference between measured levels of the antigen and normal levels may be a relative or absolute quantity. In addition, "levels of antigen" is used to mean any measure of the quantity of the antigen such as, but not limited to, mass, concentration and biological activity. Example of biological activities that may be used to quantify antigens include, but are not limited to, chemotactic, cytotoxic, enzymatic or other biological activities, such as quantifiable activities that are used, for example, by the National Institute for Biological Standards and Control (NIBSC) in the United Kingdom for the quantification of interferon, cytokine and growth-factor activity. The difference in levels of antigen may be equal to zero, indicating that the subject is or may be normal, or that there has been no change in levels of antigen since the previous assay.

The difference may simply be, for example, a measured fluorescent value, radiometric value, densitometric value, mass value etc., without any additional measurements or manipulations. Alternatively, the difference may be expressed as a percentage or ratio of the measured value of the antigen to a measured value of another compound including, but not limited to, a standard or internal standard. The difference may be negative, indicating a decrease in the amount of measured antigen over normal value or from a previous measurement, and the difference may be positive, indicating an increase in the amount of measured antigen over normal values or from a previous measurement. The difference may also be expressed as a difference or ratio of the antigen to itself, measured at a different point in time. The difference may also be determined using in an algorithm, wherein the raw data is manipulated.

In general, levels of antigen that are higher than normal levels of antigen may confirm that the subject has the abnormal condition or that the subject may have a lower probably than normal of not developing the abnormal condition. Conversely, levels of antigen that are equal to or lower than normal levels of antigen may confirm that the subject does not have abnormal condition or that the subject may have a higher probability than normal of not developing the abnormal condition.

The present invention also relates to methods of monitoring the progression of an abnormal condition in a subject. These methods comprise determining the levels of an antigen in a sample at two more time points, where the antigen comprises an amino acid sequence at least 80% to the amino acid sequence. The measured levels at each of the time points are compared to one another to determine a difference in level on antigen over time. Progression, regression or stasis of the abnormal condition may be indicated by a difference in the measured levels of the antigen in the subject over time.

As used herein, the phrase "monitor the progression" is used to indicate that the abnormal condition in the subject is being periodically checked to determine if the abnormal condition is progressing (worsening), regressing (improving) or remaining static (no detectable change) in the individual by assaying the levels of biomarker in the subject using the methods of the present invention. The methods of monitoring may be used in conjunction with other monitoring methods or treatment regimens for the abnormal condition and to monitor the efficacy of these treatments. Thus, "monitor the progression" is also intended to indicate assessing the efficacy of a treatment regimen by periodically assessing the levels of biomarker and correlating any differences in the levels of biomarker in the subject over time with the progression, regression or stasis of the abnormal condition. Thus, for example, the methods of the present invention may be used to monitor a subject after a treatment. In particular, the methods may be used to monitor patients that have had a successful treatment, such that the methods can be used to monitor the patient for follow up procedures. In another particular embodiment, the methods may be used to monitor patients that have received treatment, but may need additional or concurrent treatment. The methods can thus be used to determine a suitable follow up therapeutic regimen, after an initial treatment.

Thus, in one embodiment, the present invention provides methods of individualizing a therapeutic regimen, comprising assessing levels of biomarker and correlating these levels with a likely response to a variety of therapies. For example, patient populations may be stratified according to their response to therapy as their responsiveness correlates to levels of biomarker. Monitoring may include assessing the levels of biomarker at two time points from which a sample is taken, or it may include more time points, where any of the levels of biomarker at one particular time point from a given subject may be compared with the levels of biomarker in the same subject, respectively, at one or more other time points.

The present invention also relates to methods for determining cell proliferation rates. The methods can be used in vivo or in vitro. The methods comprise determining the levels of RGC-32 in a population of test cells and comparing the test cell levels with levels of RGC-32 in a control cell sample where the proliferation rate of the cells is known. Further, the levels of RGC-32 in the control cell population are correlated to a proliferation rate. Thus, the methods comprise determining a difference between RGC-32 in the test and control cells, where a difference in RGC-32 levels can be correlated to a proliferation rate. As used herein, a "proliferation rate" can be quantitative or qualitative. For example, the proliferation rate of cells includes a binary determination of cell proliferation or cell non-proliferation, as well as quantitative assessments, including but not limited to, cell-doubling time, rate of $^3H$ incorporation, etc. "Control levels" antigen is used to mean levels of the antigen in a population where the proliferation rate is known.

The present invention also relates to methods of identifying compounds effective in altering cell proliferation. The methods comprise administering a candidate compound to a test population of cells and assessing the levels of the biomarker of the present invention, in response to the test compound. A difference in levels of the biomarker of the present invention in treated cells versus untreated control cells may indicate that the candidate compound is effective in altering the proliferation rates of cells. For example, a candidate compound that causes an increase in the levels of biomarker over control untreated cells may increase the proliferation rates of the cells. Alternatively, a candidate compound that causes a decrease in the levels of biomarker over control untreated cells may decrease the proliferation rates of the cells.

The present invention also relates to altering cell proliferation comprising administering the compositions, e.g., an antibody, to cell. In one embodiment, the present invention relates to arresting cells in the cell cycle comprising administering an antagonist of the biomarker, e.g., an antibody, of the present invention to cells. Likewise, the present invention relates to increasing cell proliferation comprising administering the biomarker of the present invention, or agonists thereof, to cells.

The cells that may be assayed or may be the target for therapeutic intervention include any type of cell. Examples of such cells include but are not limited to, epithelial cells, endothelial cells, epithelial cells, osteoblasts, chondrocytes, myocytes, adipocytes, muscle cells, neuronal cells, lymphocytes (e.g., b-cells, T-cells etc.), phagocytes and even stem cells and progenitor cells.

The compositions described herein can be administered in vitro, ex vivo, or in vivo to cells which express the biomarker of the present invention. By administration of an "effective amount" of an agonist or antagonist is intended an amount of the compound that is sufficient to enhance or inhibit a cellular response to the biomarker of the present invention. In particular, by administration of an "effective amount" of an agonist or antagonists is intended an amount effective to enhance or inhibit biomarker-mediated cell proliferation. Of course, where it is desired for cell proliferation to be enhanced, an agonist according to the present invention can be co-administered with another compound. One of ordinary skill will appreciate that effective amounts of an agonist or antagonist can be determined empirically and may be employed in pure form or in pharmaceutically acceptable salt, ester or prodrug form. The agonist or antagonist may be administered in compositions in combination with one or more pharmaceutically acceptable excipients (i.e., carriers).

The invention thus provides methods of treatment, inhibition and prophylaxis of an abnormal condition comprising administering to a subject of an effective amount of a compound or pharmaceutical composition of the invention. In one embodiment, the therapeutic is an antibody of the invention.

Formulations and methods of administration that can be employed when the compound comprises a nucleic acid or an immunoglobulin are described above; additional appropriate formulations and routes of administration can be selected from among those described herein below.

It will be understood that, when administered to a human patient, the total daily usage of the compounds and compositions of the present invention will be decided by the attending physician within the scope of sound medical judgment. The specific therapeutically effective dose level for any particular patient will depend upon factors well known in the medical arts.

As a general proposition, the total pharmaceutically effective amount of, for example an RGC-32 antagonist, administered parenterally per dose will be in the range of about 1 μg/kg/day to 10 mg/kg/day of patient body weight, although, as noted above, this will be subject to therapeutic discretion. In particular, this dose is at least 0.01 mg/kg/day. If given continuously, the agonists or antagonists of antagonists of the present invention are typically administered at a dose rate of about 1 μg/kg/hour to about 50 μg/kg/hour, either by 14 injections per day or by continuous subcutaneous infusions, for example, using a mini-pump. An intravenous bag solution may also be employed.

Dosaging may also be arranged in a patient specific manner to provide a predetermined concentration of an agonist or antagonist in the blood, as determined by the RIA technique. Thus patient dosaging may be adjusted to achieve regular on-going trough blood levels, as measured by RIA, on the order of from 50 to 1000 ng/ml, in particular about 150 to 500 ng/ml.

Pharmaceutical compositions are provided comprising an agonist or antagonist and a pharmaceutically acceptable carrier or excipient, which may be administered orally, rectally, parenterally, intracisternally, intravaginally, intraperitoneally, topically (as by powders, ointments, drops or transdermal patch), bucally, or as an oral or nasal spray. Importantly, by co-administering an agonist and an addition effective compound, clinical side effects can be reduced by using lower doses of both the ligand and the agonist. It will be understood that the agonist can be "co-administered" either before, after, or simultaneously with the antagonists of the present invention, depending on the exigencies of a particular therapeutic application. By "pharmaceutically acceptable carrier" is meant a non-toxic solid, semisolid or liquid filler, diluent, encapsulating material or formulation auxiliary of any type. In a specific embodiment, "pharmaceutically acceptable" means approved by a regulatory agency of the federal or a state government or listed in the U.S. Pharmacopeia or other generally recognized pharmacopeia for use in animals, and more particularly humans. The term "carrier" refers to a diluent, adjuvant, excipient, or vehicle with which the therapeutic is administered. Such pharmaceutical carriers include, but are not limited to, sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include, but are not limited to, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In one embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The term "parenteral" as used herein refers to modes of administration which include intravenous, intramuscular, intraperitoneal, intrasternal, subcutaneous and intraarticular injection and infusion.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, 1987, *J. Biol. Chem.* 262:4429-4432), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter; by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, (1989).

In yet another embodiment, the compound or composition can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (1990, Science 249:1527-1533). The compositions of the invention are also suitably administered by sustained-release systems. Suitable examples of sustained-release compositions include suitable polymeric materials (such as, for example, semi-permeable polymer matrices in the form of shaped articles, e.g., films, or microcapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman, U. et al., Biopolymers 22:547-556 (1983)), poly (2-hydroxyethyl methacrylate) (R. Langer et al., J. Biomed Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP 133,988).

Sustained-release compositions also include liposomally entrapped compositions of the invention (see generally, Langer, Science 249:1527-1533 (1990); Treat et al., in Liposomes in the Therapy of Infectious Disease and Cancer, Lopez-Berestein and Fidler (eds.), Liss, New York, pp. 317-327 and 353-365 (1989)). Liposomes containing DR5 polypeptide my be prepared by methods known per se: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal DR5 polypeptide therapy.

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

In yet an additional embodiment, the compositions of the invention are delivered by way of a pump (see Langer, supra; Sefton, CRC Crit. Ref Biomed. Eng. 14:201 (1987); Buchwald et al., Surgery 88:507 (1980); Saudek et al., N. Engl. J. Med. 321:574 (1989)).

Pharmaceutical compositions of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use.

The compounds or pharmaceutical compositions of the invention may be tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

The compositions of the invention may be administered alone or in combination with other adjuvants. Adjuvants that may be administered with the compositions of the invention include, but are not limited to, alum, alum plus deoxycholate (ImmunoAg), MTP-PE (Biocine Corp.), QS21 (Genentech, Inc.), BCG, and MPL. In a specific embodiment, compositions of the invention are administered in combination with alum. In another specific embodiment, compositions of the invention are administered in combination with QS-21. Further adjuvants that may be administered with the compositions of the invention include, but are not limited to, Monophosphoryl lipid immunomodulator, Adju Vax 100a, QS-18, CRL1005, Aluminum salts, ME-59, and Virosomal adjuvant technology.

The compositions of the invention may be administered alone or in combination with other therapeutic agents. Therapeutic agents that may be administered in combination with the compositions of the invention, include but are not limited to, chemotherapeutic agents, antibiotics, antivirals, steroidal and non-steroidal anti-inflammatories, conventional immunotherapeutic agents, cytokines, chemokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The examples below are meant to illustrate various embodiments of the present invention and are not intended to limit the scope of the invention.

EXAMPLES

Example 1

RGC-32 mRNA Expression in Cancer Cell Lines

A 300-bp EcoRI restriction fragment from cDNA clone ID 276560 yy4 (ATCC, Rockville, Md.), which contains part of human RGC-32 sequence was used to detect RGC-32 mRNA expression. A 1.4-kb HindIII fragment of β-actin cDNA was used as a loading control. The cDNA probes were labeled with [$\alpha$-$^{32}$P]dCTP (New England Nuclear, Boston, Mass.) using an oligolabeling kit from Amersham Biosciences (Piscataway, N.J.) (See Badea, T. et al., *J. Biol. Chem.* 277:502-508 (2005)).

Figure 1B:
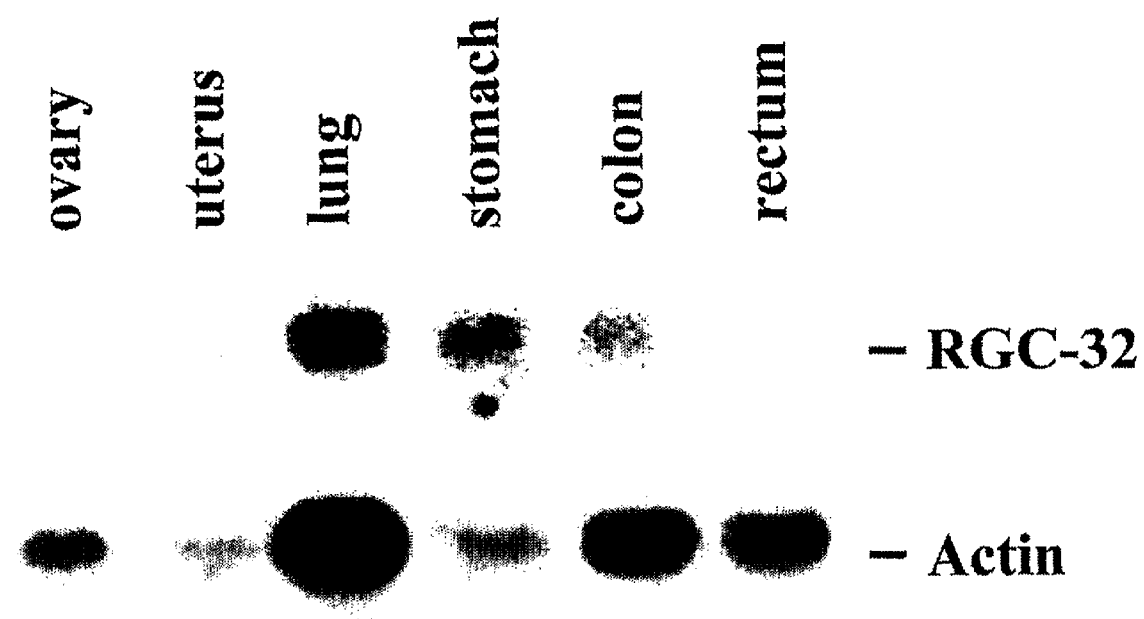

Pre-made blots from BD Biosciences Clontech (Palo Alto, Calif.) that contain 2 μg of poly A+RNA from cancer cell lines (Human Cancer Cell Line MTN Blot II) (FIG. 1A) and 10 μg of total RNA from cancer tissues (Human Tumor MTN Blot) (FIG. 1B) were analyzed for RGC-32 mRNA expression. $^{32}$P-labeled probes for RGC-32 or β-actin were hybridized to the blots overnight at 37° C. After extensive washing at 55° C., the membranes were examined by autoradiography. Lung, stomach and colon tumor tissues, exhibited the highest levels of expression for RGC-32, while ovary, uterus and rectum showed moderate to low levels of RGC-32 expression.

Figure 2A:
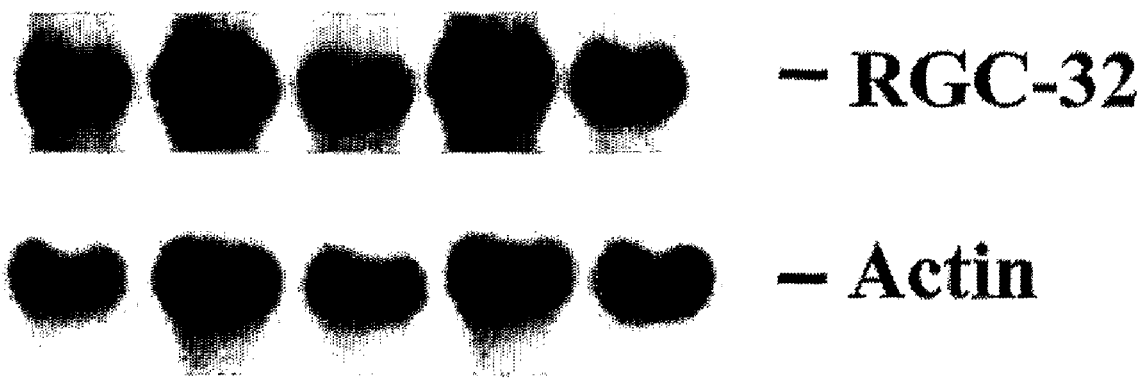
FIG. 2 depicts mRNA levels and protein levels of RGC-32 in colon adenocarcinoma. (A) Total RNA was extracted from tumor samples from five patients with colon cancer and 10 µg were loaded onto an agarose-formaldehyde gel. After fractionation by electrophoresis, RNA was immobilized on a nitrocellulose membrane and hybridized with $^{32}$[P]-labeled RGC-32 or β-actin cDNA probe. All samples tested expressed RGC-32 mRNA. (B) Colon adenocarcinoma tissues were examined for RGC-32 protein expression, using methods described herein. Tissue lysates were analyzed by 10% SDS-PAGE and Western blotting using an anti-RGC-32 IgG of the present invention. Immunoreaction was visualized by ECL and autoradiography. Heart total protein lysate was used as positive control. Both samples of colon carcinomas exhibited RGC-32 protein expression.

Colon cancer biopsy samples were frozen in liquid nitrogen and ground using a mortar and pestle. The resulting powdered tissue was treated using RNA lysis buffer containing guanidine isothiocyanate and β-mercaptoethanol (See Rus, H. et al., J. Immunol. 156:4892-4900 (1996), which is incorporated by reference). RNA was purified by uacentrifugation through a 5.7 M CsCl$_2$ cushion for 18 h at 35,000 rpm using an SW60 Beckman rotor (Beckman, Palo Alto, Calif.). RNA was denatured and electrophoresed (10 μg of RNA/lane) on 0.8% agarose-formaldehyde gel and then transferred to nitrocellulose membrane. RNA was fixed onto the membrane by baking for 2 h at 80° C. (Rus, H. et al., J. Immunol. 156:4892-4900 (1996)). The nitrocellulose membrane was hybridized overnight at 37° C. with $^{32}$P-labeled specific cDNA probe. After serial washings at 55° C., the membrane was exposed to x-ray film. Radiographic densities of each mRNA band were measured, and the integrated volume was calculated using UnScanIt software (Silk Scientific, Orem, Utah). (FIG. 2A).

Example 2

Expression Array Analysis of RGC-32 in Tumor and Normal Tissue

The Matched Tumor/Normal Expression Array (Clontech, Palo Alto, Calif.) allowed us to compare the expression of RGC-32 in a variety of tumor samples. This array contains 50 ng of cDNA synthesized from 68 human tumors and corresponding normal tissue spotted on a nylon membrane. The array was pre-hybridized with ExpressHyb buffer (BD Biosciences Clontech) containing 1 mg/ml of heat-denatured sheared salmon DNA (Sigma-Aldrich, St. Louis Mo.). RGC-32 cDNA was radiolabelled with [$\alpha$-$^{32}$P]dCTP then mixed with sheared salmon DNA and 20×SSC. The probe was then heated to 100° C. for 5 min then to 68° C. for 30 min. The denatured probe was added to fresh ExpressHyb buffer and allowed to hybridize with the array overnight at 65° C. After extensive washing at 65° C., the array was exposed to X-ray film. As a housekeeping gene, cDNA for ubiquitin was radiolabelled with [$\alpha$-$^{32}$P]dCTP and hybridized in the same manner as RGC-32. The density of each spot was measured by UnScanIt software and RGC-32 expression was normalized to ubiquitin.

All tissues, both normal and cancerous, expressed RGC-32. In general, RGC-32 was upregulated 19% in tumor tissue over adjacent normal tissue. In some cases, increase in RGC-32 mRNA expression was associated with metastasis. The number of samples that showed a greater than 2-fold increase in RGC-32 expression in tumor vs. normal tissue is shown in Table 2. "N/A" denotes that information on metastasis was not supplied.

TABLE 1

| Tumor type | Number of cases | Number of tumors with >2 fold expression of RGC-32 over normal tissues | Cases of >2 fold in RGC-32 exhibiting metastases |
| --- | --- | --- | --- |
| Kidney | 15 | 5 | 0 |
| Colon | 11 | 2 | 2 |
| Stomach | 11 | 3 | 1 |
| Rectum | 7 | 1 | 1 |
| Ovary | 3 | 1 | N/A |
| Small intestine | 1 | 1 | N/A |

Example 3

PCR of Matched cDNA Samples

To confirm the results of the Matched Tumor/Normal Expression Array and to verify that RGC-32 gene was expressed in colon tumors, one set of Matched cDNA Pairs (BD Biosciences Clontech-catalog #: 7840-1) was tested for RGC-32 expression by PCR. For PCR, 15 ng of cDNA from tumor or normal tissue were amplified for RGC-32 using forward primer: 5'-GCCACTTCCACTACGAGGAG-3' (SEQ ID NO: 4) and reverse primer: 5'-GTGGCCTGGTA-GAAGGTTGA-3' (SEQ ID NO: 5). The amplification consisted of an initial denaturation of 95° C. for 5 min, 31 cycles of 95° C. for 1 min, 60° C. for 1 min, 72° C. for 1 min followed by a 5 min extension at 72° C. Human Ribosomal Protein S9 was used for normalization of the RGC-32 expression using control primers included with the Matched cDNA pair kit (Clontech). The S9 amplification consisted of an initial denaturation at 94° C. for 30 sec, 25 cycles of 94° C. for 30 sec, and 68° C. for 2 min followed by one cycle of 68° C. for 5 min. PCR products were analyzed on a 1.5% agarose gel and bands were quantified by densitometric scanning using UnScanit software. This PCR analysis confirmed that the expression of RGC-32 was increased 1.6 fold in the tumor tissue sample versus normal tissue (data not shown).

Example 4

Preparation of Anti-RGC-32 Antibody

The RGC-32 open reading frame (ORF) was subcloned in pGEX-4T-3 vector (Pharmacia, Piscataway, N.J.) in frame with the GST gene. Recombinant fusion protein (GST-RGC-32) extracted from bacterial lysates was purified by chromatography using Redipack GST purification module (Pharmacia). Antibodies were raised against a specific peptide sequence (SEQ ID NO:1), which was selected through hydrophobicity analysis, by immunization of rabbits as previously described in Badea, T. et al., *J. Biol. Chem.* 277:502-508 (2005). Screening of IgG affinity purified fraction from the antisera was performed by Western blotting (See Badea, T. et al., *J. Biol. Chem.* 277:502-508 (2005)). The prepared antibody binds to the recombinant GST-RGC-32 protein.

Example 5

Western Blot Analysis of RGC-32 in Cancer Tissue

Figure 2B:
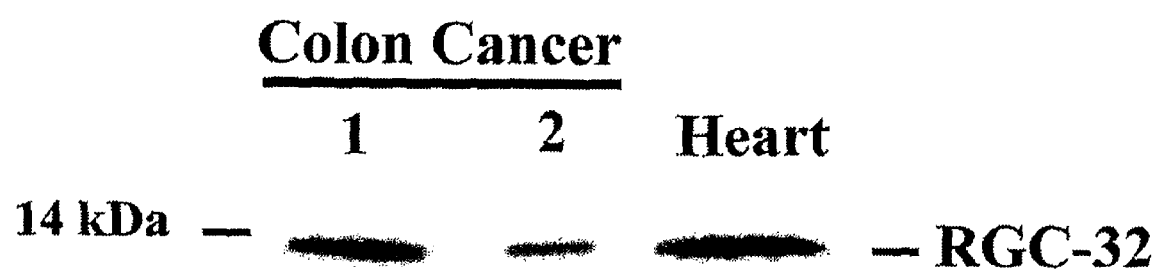

Colon cancer samples were ground in liquid nitrogen with a mortar and pestle. The tissue was lysed in RIPA buffer and processed as previously described in Niculescu, F., et al. *J. Immunol.*, 158:4405-4412 (1997), which is incorporated by reference). Total protein (100 µg) was pre-cleared with protein A/G agarose (Santa Cruz Biotechnology, Santa Cruz, Calif.) for 1 h at 4° C. To the pre-cleared lysate, 1.5 µg of affinity purified anti-RGC-32 antibody and 20 µl of protein A/G agarose were added and incubated overnight at 4° C. The immunoprecipitated protein, 100 µg of Heart Protein Medley (BD Biosciences Clontech) or 3 µg of recombinant RGC-32-GST fusion protein were electrophoresed through a 10% SDS-PAGE gel and transferred to nitrocellulose membrane. The membrane was then incubated with anti-RGC-32 antibody followed by anti-rabbit HRP conjugated antibody. The signal was visualized by enhanced chemiluminescence (ECL, Pierce, Rockford, Ill.) and autoradiography. Heart total protein lysate was used as positive control. Both samples of colon carcinomas exhibited RGC-32 protein expression. (FIG. 2B).

Example 6

Immunohistochemistry Analysis of RGC-32 Localization

Indirect immunoperoxidase was performed on MaxArray Human Multi-Tumor Tissue Microarray Slides and MaxArray Colon Carcinoma/Normal Tissue Microarray Slides (Zymed Laboratories, San Francisco, Calif.) and with adenocarcinoma and normal colorectal tissue slides from ψPro Sci Incorporated (Poway, Calif.). Each MaxArray Human Multi-Tumor Tissue Microarray slides contains 60 malignant tumor tissue cores. The list of tumor tissues on the MaxArray is available on the world-wide web at www.zymed.com. The MaxArray Colon carcinoma/Normal contained 20 colon carcinomas (18 adenocarcinomas and 2 mucinous carcinomas) and matched adjacent and remote mucosa.

Normal and colon adenocarcinoma tissue sections stained for RGC-32, using an antibody of the present invention, by indirect immunoperoxidase. Briefly, paraffin sections containing neoplastic areas and normal tissue were deparaffinized in xylene according to standard procedures followed by rehydration through a graded ethanol series. Then the sections were washed in PBS and endogenous peroxidase was quenched with 3% hydrogen peroxide in PBS for 5 min. Slides were washed and incubated overnight at 4° C. with the rabbit polyclonal anti-RGC-32 diluted 1:50 in PBS, then with goat anti rabbit HRP conjugated IgG (Jackson ImmunoResearch Labs, West Grove, Pa.) for 1 hr at room temperature. The reaction was developed using Nova RED (Vector Labs) as a chromogen substrate then the sections were washed in distilled water and counterstained with Harris's hematoxylin (Sigma) and mounted with permanent mount. All sections were counterstained with Hematoxylin (960×). The immunostaining was evaluated by two pathologists in a blinded fashion.

Figure 3:
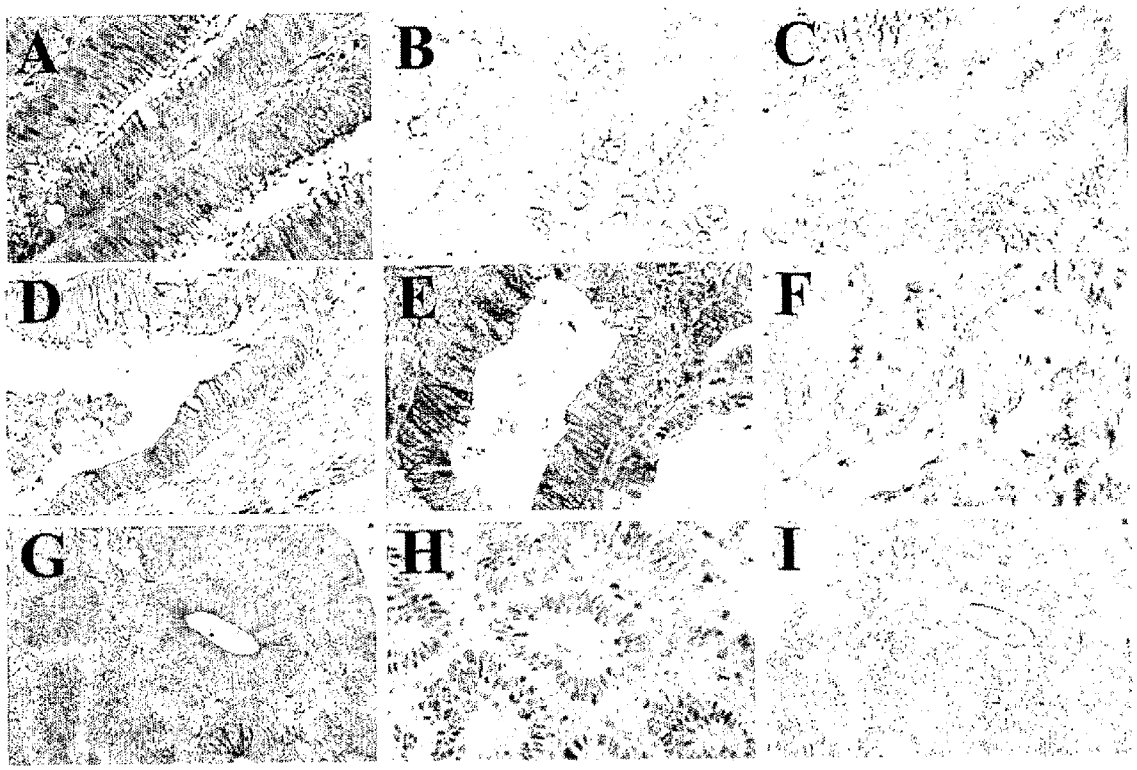
FIG. 3 depicts immunostaining for RGC-32 and Ki-67 in normal colon and adenocarcinoma. Normal and colon adenocarcinoma tissue sections stained for RGC-32, using an antibody of the present invention, by indirect immunoperoxidase. Malignant epithelial cells were strongly reactive for RGC-32 (A), whereas normal colonic epithelium was consistently negative (B and C). Occasionally, however, some normal colon samples showed immunoreactivity to interstitial mesenchymal cells (C). Tumors showed two major patterns of immunoreactivity. In some carcinomas, only the malignant epithelial cells were reactive for RGC-32 (D), while both the malignant epithelia as well as the cells in the interstitium were positive in others (E). In some instances, staining of tumors showed a patchy pattern (F). Consecutive sections were stained for RGC-32 and Ki-67 (G and H). The nuclear staining of Ki-67 (H) showed co-localization with the RGC-32 staining (G). Corresponding section stained with IgG isotype control showed negative reactivity (I). All sections were counterstained with Hematoxylin (960×).

Malignant epithelial cells were strongly reactive for RGC-32 (FIG. 3A), whereas normal colonic epithelium was consistently negative (FIGS. 3B and 3C). Occasionally, however, some normal colon samples showed immunoreactivity to interstitial mesenchymal cells (FIG. 3C). Tumors showed two major patterns of immunoreactivity. In some carcinomas, only the malignant epithelial cells were reactive for RGC-32 (FIG. 3D), while both the malignant epithelia as well as the cells in the interstitium were positive in others (FIG. 3E). In some instances, staining of tumors showed a patchy pattern (FIG. 3F). Consecutive sections were stained for RGC-32 and Ki-67 (FIGS. 3G and 3H). The nuclear staining of Ki-67 (FIG. 3H) showed co-localization with the RGC-32 staining (FIG. 3G). Corresponding section stained with IgG isotype control showed negative reactivity (FIG. 3I).

Figure 4:
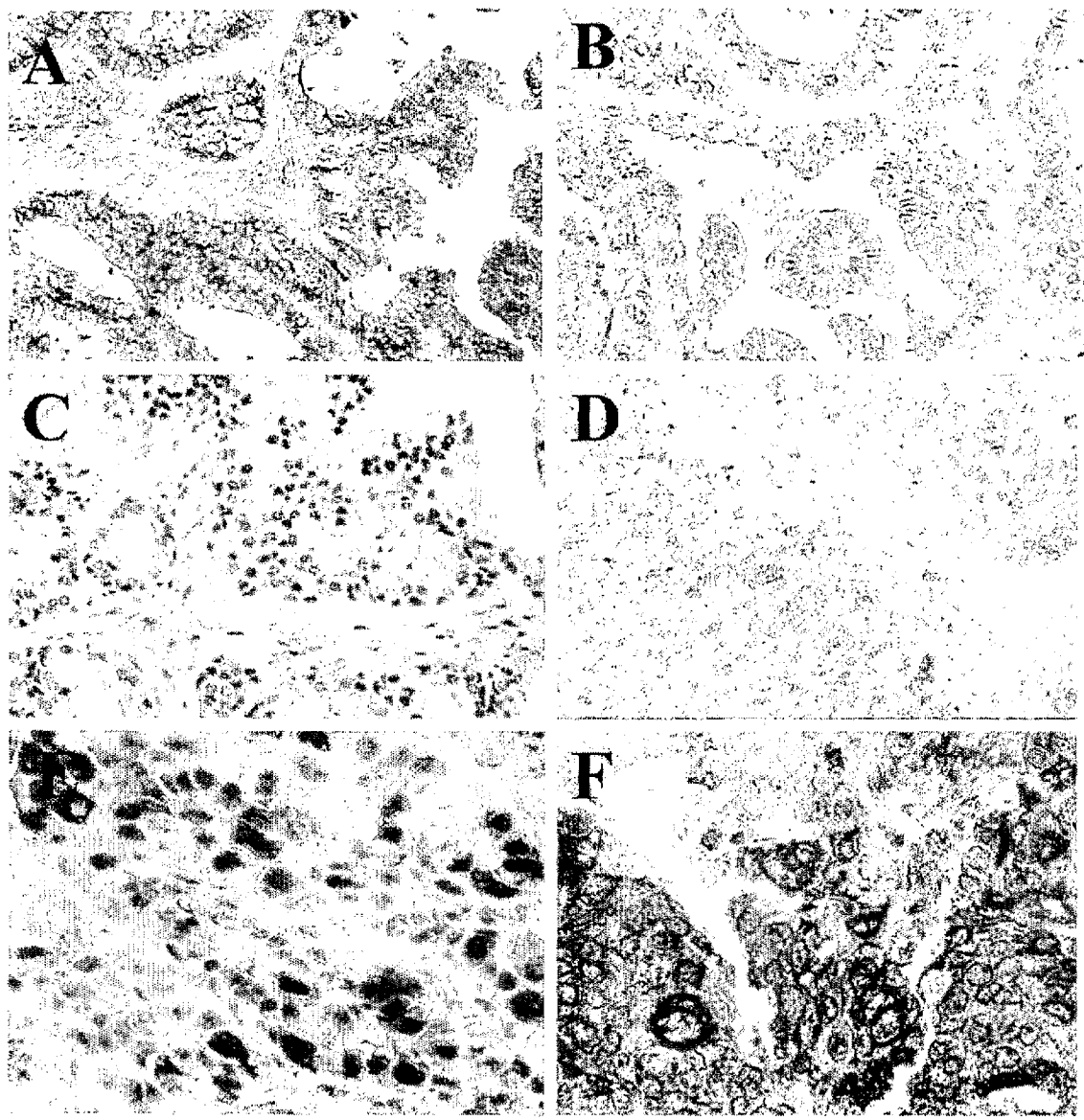
FIG. 4 depicts immunostaining for RGC-32 and Ki-67 in cancers of various organs. Indirect immunoperoxidase staining for RGC-32 was performed on various carcinomas using an antibody of the present invention. Strong immunoreactivity was found in prostate (A), lung (E), and esophageal (F) tumors, and moderate reactivity was seen in a gastric tumor (D). In a consecutive section of prostate adenocarcinoma, nuclear staining of Ki-67 was observed in tumor cells (C) that were stained for RGC-32 (A). Control stain for Ki-67 showed negative reactivity (B). All sections were counterstained with Hematoxylin (960×).

Strong immunoreactivity was found in prostate (FIG. 4A), lung (FIG. 4E), and esophageal (FIG. 4F) tumors, and moderate reactivity was seen in a gastric tumor (FIG. 4D). In a consecutive section of prostate adenocarcinoma, nuclear staining of Ki-67 was observed in tumor cells (FIG. 4C) that were stained for RGC-32 (A). Control stain for Ki-67 showed negative reactivity (FIG. 4B).

Example 6

Localization of RGC-32 in Brain Tissue

Frozen brain tissue specimens were obtained at autopsy from seven patients with a definite diagnosis of multiple sclerosis from the Human Brain and Spinal Fluid Resource Center, VA West Los Angeles Health Care Center, Los Angeles, Calif. The active lesions contained abundant inflammatory cell infiltrates consisting of T cells and macrophages with detectable myelin degradation products. Acute active lesions contained inflammatory cells throughout the entire lesion, whereas the inflammation was restricted to the lesion margins in chronic active lesions. Regions of non-lesion white matter (NLWM) and non-lesion gray matter (NLGM) that lacked macroscopic or histological evidence of demyelination were also used. The samples were derived from patients between the ages of 30-51 with a mean of 44.

Human peripheral blood mononuclear cells (PBMC) were purified from whole blood as described previously (Rus, H. et al., *Proc. Natl. Acad. Sci. USA* 2005, 102, 11094-11099). Cells were separated by centrifugation and stained as described below.

Cryosections were fixed in acetone containing 0.3% peroxide were incubated with rabbit polyclonal against RGC-32 (diluted 1/50), for 2 h at RT, then incubated for 1 h with goat anti-rabbit HRP-conjugated IgG. Specific reaction was developed using NovaRED (Vector Labs, Burlingame, Calif.). Nuclei were counterstained with Harris's hematoxylin (Sigma, St. Louis, Mo.). Controls were prepared by immunostaining without the primary antibody. A similar indirect immunoperoxidase technique was used for CD3 and CD68 staining.

Double staining was performed as previously described (Rus H. et al., Proc. Natl. Acad. Sci. USA 2005, 102, 11094-11099). Cryosections were immunostained for RGC-32, as described above, then further incubated with either anti-CD68 or anti-CD3, followed by HRP-conjugated secondary antibody and reacted with DAB (Pierce, Rockford, Ill.).

Figure 6:
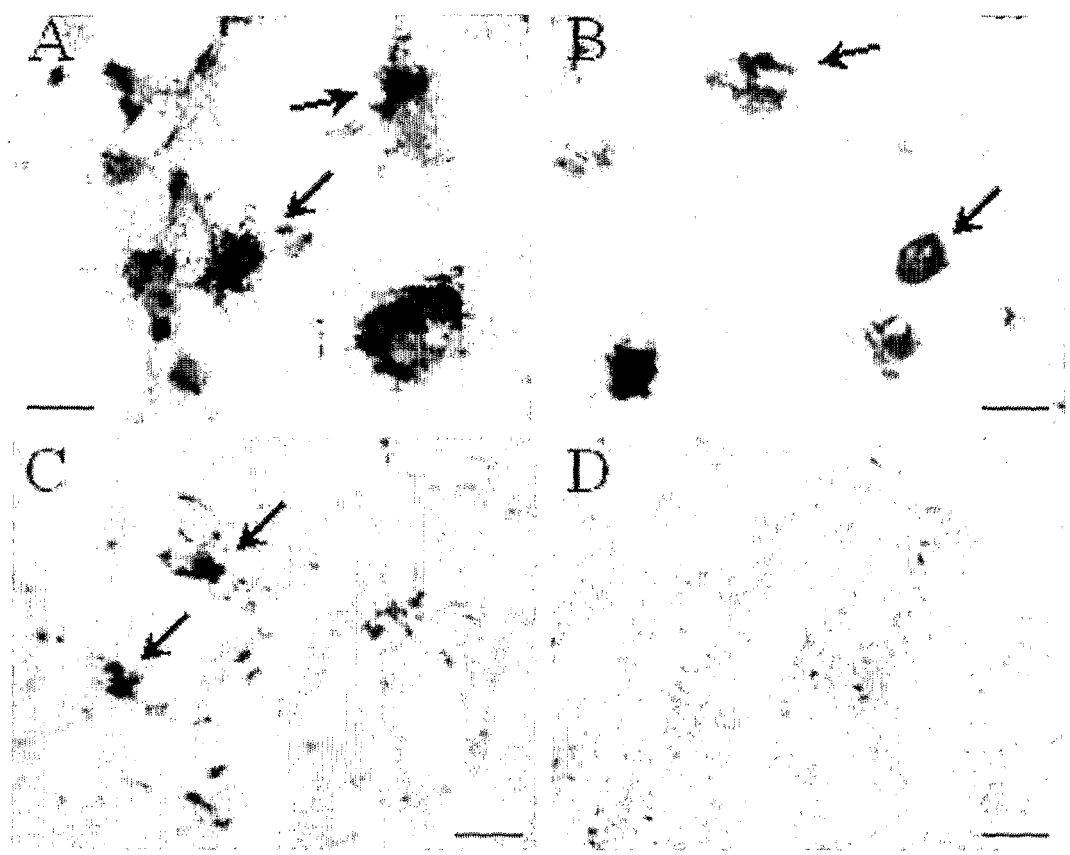
FIG. 6 depicts colocalization of RGC-32 with CD3 and CD68 positive inflammatory infiltrates in multiple sclerosis brain. MS plaques cryostat sections were examined for RGC-32 and CD3 or CD68 by double labeling. (A) Double labeling identified some RGC-32+ cells as CD3+ cells (red-RGC-32, dark-brown-CD3); not all CD3 cells expressed RGC-32. (B) Double labeling with RGC-32 (red) and CD68 (dark-brown) was also clearly seen. Inserts show double labeled cells at higher magnification. (C) CD68+ cells with glial morphology also display RGC-32. (D) Control of the immunoperoxidase reaction. Scale bar=20 µm.
Figure 7:
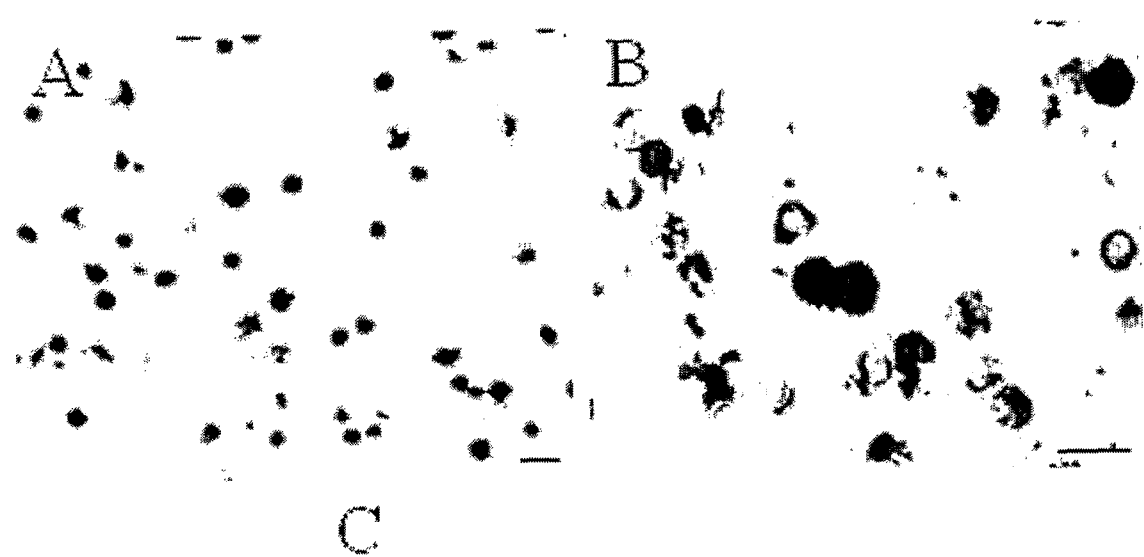
FIG. 7 depicts expression of RGC-32 in peripheral blood mononuclear cells (PBMC). PBMC from patients with relapsing remitting multiple sclerosis were immunostained for RGC-32 expression using indirect immunoperoxidase. (A and B) Many of PBMC express RGC-32 in patients with relapsing remitting MS. (C) Control of immunoperoxidase reaction. Scale bar=20 µm.

We performed immunohistochemical analysis on 20 different areas of grossly involved white matter plaques and areas of grossly uninvolved tissue (Table 2 and FIGS. 6 and 7).

Figure 5:
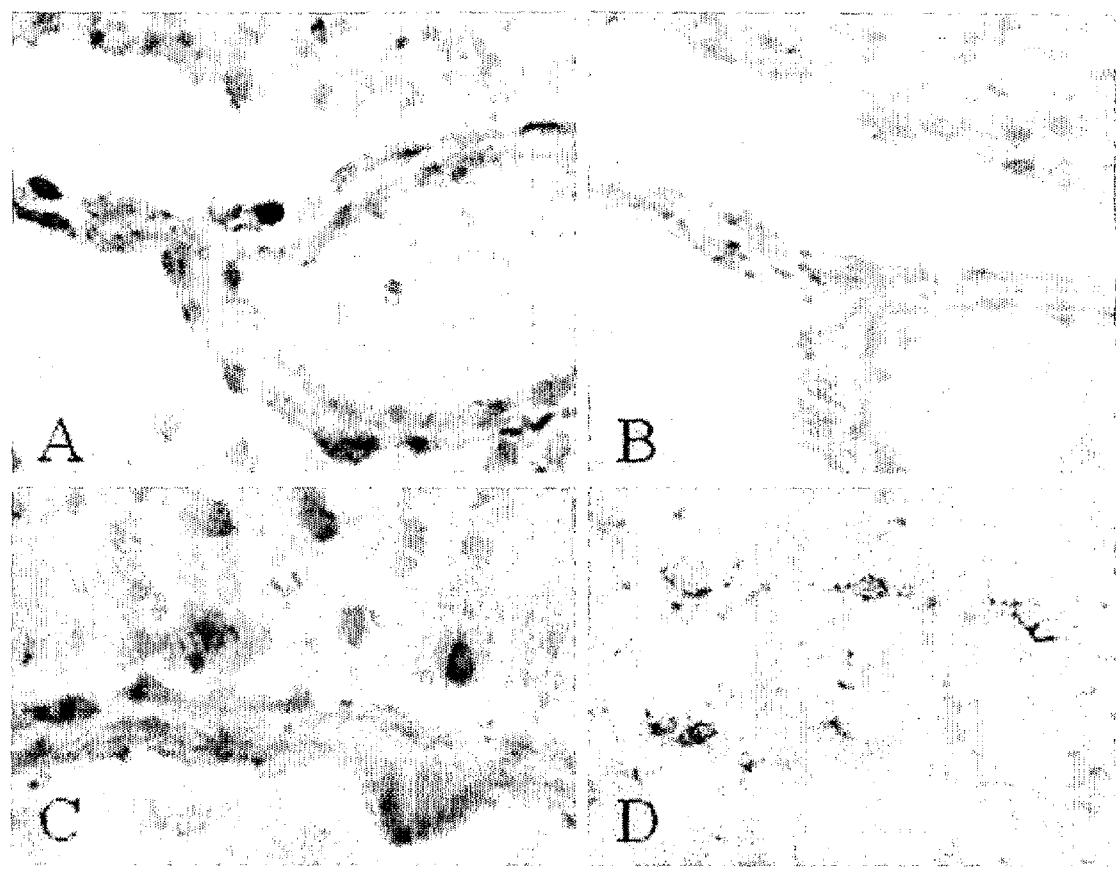
FIG. 5 depicts expression of RGC-32 on inflammatory cells in multiple sclerosis (MS) brain. Cryostat sections were stained by indirect immunoperoxidase for RGC-32. Areas used in sectioning were from a white matter plaque (A-C) and a non-lesion gray matter (NLGM) area (D). There were many perivascular inflammatory cells that stained positively for RGC-32 (A, C). RGC-32 was also localized to inflammatory cells in the white matter parenchyma. (B). Control of the immunoperoxidase reaction.

5C). In addition, RGC-32 was expressed in the parenchymal infiltrate of the majority of MS plaques (FIG. 5D). Serial sections through areas of intense RGC-32 staining on lymphocytes revealed an absence of CCR7 (data not shown), but positive CCR5 staining on some of the infiltrating cells. CCR7 was routinely detected on peripheral blood cytospins using the same antibody (data not shown) and was rarely detected on perivascular cells. These RGC-32+ cells are therefore activated TEM cells (CCR7−). Many of these cells were RGC-32+ inflammatory cells in apparently normal white and gray matter (FIG. 5C). Many of these cells were CD68+ mononuclear cells (FIG. 6B). Some of the inflammatory cells had morphology suggestive of ramified microglia (FIG. 6C) and in double labeling experiments some but not all of the CD68+ cells also expressed RGC-32 (FIG. 6B). Most RGC-32+ cells, however, were also positive for CD3 (FIG. 6A). No background staining could be detected using isotype control primary antibodies (FIG. 6D).

We also examined PBMC samples derived from three MS patients with a relapsing remitting pattern. Many of the PBMCs expressing RGC-32 (FIG. 7) were also CD3 or CD68 positive.

TABLE 2

| | | | | | | RGC32 expression | |
|---|---|---|---|---|---|---|---|
| Case | Sex | Age | Lesion types | No. of lesions | Lesional activity | Perivascular infiltrate | Parenchimal infiltrate/microglia |
| 1 | F | 47 | Frontal plaque | 3 | Chronic active | ++/+++ | + |
| | | | | | Nonlesional WM | ++ | +/++ |
| | | | | | Nonlesional GM | + | ++ |
| 2 | M | 50 | Frontal plaque | 1 | Nonlesional GM | ++/+++ | − |
| 3 | M | 50 | Temporal plaque | 3 | Acute | ++ | ++/+++ |
| | | | | | Nonlesional WM | +/++ | ++ |
| | | | | | Nonlesional GM | +−rare | + |
| 4 | M | 50 | Occipital Plaque | 1 | Nonlesional WM | +/++ | +++ |
| 5 | F | 51 | Frontal plaque | 3 | Acute | ++ | ++ |
| | | | | | Nonlesional WM | ++ | +++ |
| | | | | | Nonlesional GM | ++ | ++ |
| 6 | F | 51 | Occipital Plaque | 3 | Chronic active | ++/+++ | ++/+++ |
| | | | | | Nonlesional WM | ++/+++ | ++/+++ |
| | | | | | Nonlesional GM | ++ | + |
| 7 | F | 38 | Parietal plaque | 3 | Chronic active | ++ | ++ |
| | | | | | Nonlesional MW | + | +/++ |
| | | | | | Nonlesional GW | + | + rare |
| 8 | F | 38 | Occipital Plaque | 3 | Chronic active | +++ | +++ |
| | | | | | Nonlesional WM | +++ | +++ |
| | | | | | Nonlesional GM | ++ | ++ |

Figure 8:
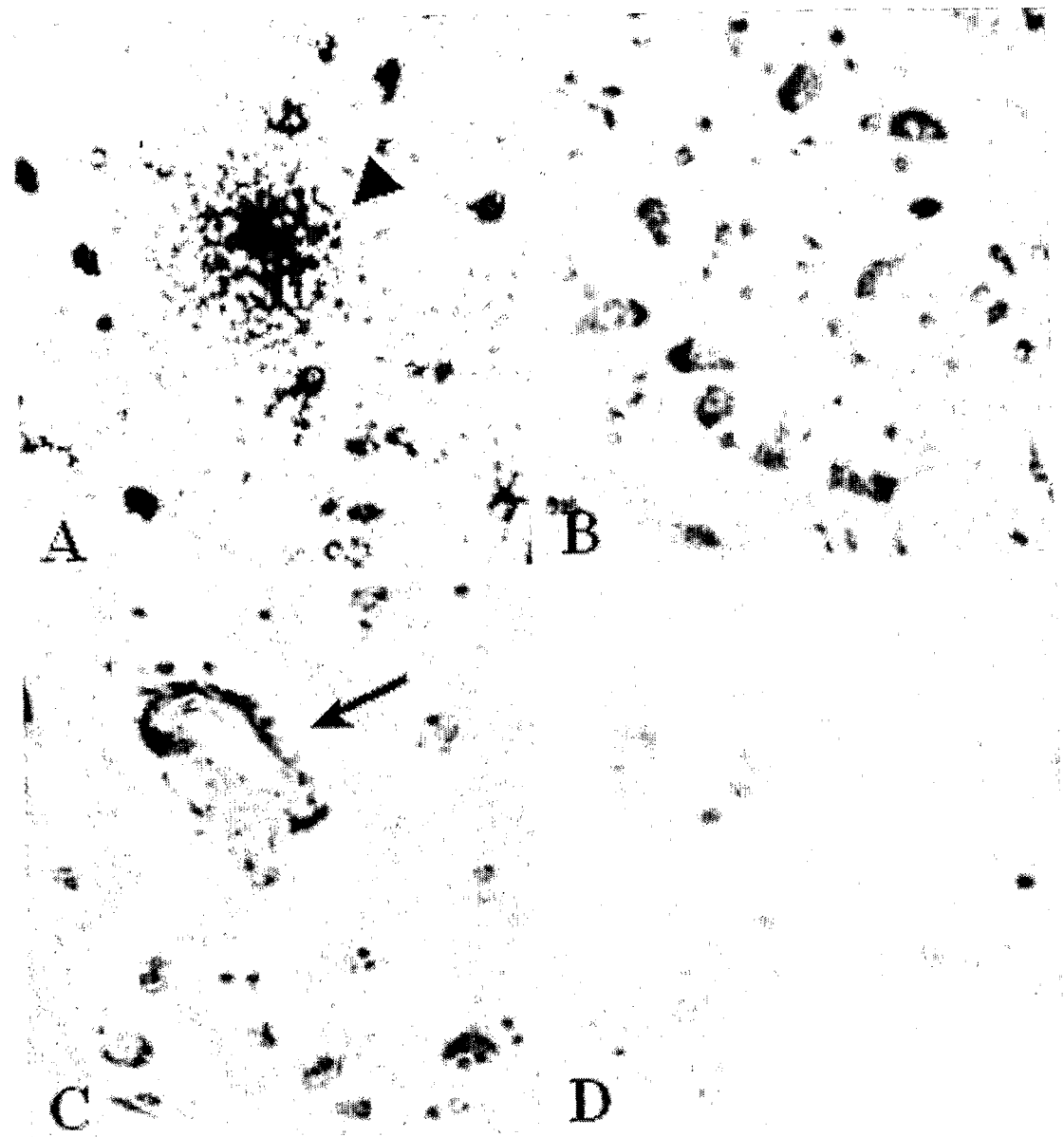
FIG. 8 depicts expression of RGC-32 in Alzheimer's brain. Cryostat sections were stained by indirect immunoperoxidase for RGC-32. RGC-32 was localized on neuritic plaques (arrowhead) (A), dystrophic neurons (B, C) and blood vessels (arrow) (C). Control sections were negative for staining (D).

F, female; M, male; WM white matter, GM, gray matter, − negative, + slightly positive, ++, positive, +++, highly positive As expected, we found a predominance of CD3+/CD4+ T cells in the perivenular infiltrate (data not shown). Many, but not all, of these cells stained positively for RGC-32 (FIG. 5A, We examined brains multiple areas from the brains of 2 patients with Alzmeimer disease. RGC-32 was found on neuritic plaques, dystrophic neurons and blood vessels (FIG. 8).

What is claimed is:

1. An isolated antibody that specifically binds to the amino acid sequence of SEQ ID NO:1, wherein said antibody is a monoclonal antibody.

2. The antibody of claim 1, wherein said antibody is a single chain antibody.

3. The antibody of claim 1, wherein said antibody is a single chain Fv (scFv) fragment.

4. The antibody of claim 1, wherein said antibody is a Fab fragment.

5. The antibody of claim 1, wherein said antibody is a humanized antibody.

6. The antibody of claim 1, wherein said antibody is a chimeric antibody.

7. A composition comprising the antibody of claim 1 and a carrier.

8. A method of detecting an antigen in a biological sample, said method comprising contacting said biological sample with the antibody of claim 1, and detecting the binding of said antibody to said antigen, wherein detectable binding is indicative of the presence of said antigen in said biological sample.

9. The method of claim 8, wherein said antibody is a single chain antibody.

10. The method of claim 8, wherein said antibody is a single chain Fv (scFv) fragment.

11. The method of claim 8, wherein said antibody a Fab fragment.

12. The method of claim 8, wherein said antibody a humanized antibody.

13. The method of claim 8, wherein said antibody a chimeric antibody.

* * * * *